US008940265B2

(12) United States Patent
McAlister

(10) Patent No.: US 8,940,265 B2
(45) Date of Patent: Jan. 27, 2015

(54) SUSTAINABLE ECONOMIC DEVELOPMENT THROUGH INTEGRATED PRODUCTION OF RENEWABLE ENERGY, MATERIALS RESOURCES, AND NUTRIENT REGIMES

(75) Inventor: Roy E. McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 0 days.

(21) Appl. No.: 12/857,553

(22) Filed: Aug. 16, 2010

(65) Prior Publication Data
US 2011/0061295 A1  Mar. 17, 2011

Related U.S. Application Data

(63) Continuation-in-part of application No. 12/707,651, filed on Feb. 17, 2010, now Pat. No. 8,075,748, and a continuation-in-part of application No. 12/707,653, filed on Feb. 17, 2010, now Pat. No. 8,172,990, and a continuation-in-part of application No. 12/707,656, filed on Feb. 17, 2010, now Pat. No. 8,075,749.

(60) Provisional application No. 61/153,253, filed on Feb. 17, 2009, provisional application No. 61/237,476, filed on Aug. 27, 2009, provisional application No. 61/304,403, filed on Feb. 13, 2010, provisional application No. 61/345,053, filed on May 14, 2010.

(51) Int. Cl.
*F02B 43/08* (2006.01)
*C01B 31/02* (2006.01)
*C10B 47/00* (2006.01)

(52) U.S. Cl.
CPC ............... *F02B 43/08* (2013.01); *Y02T 10/166* (2013.01); *Y02T 10/32* (2013.01); *Y02C 20/20* (2013.01); *Y02E 10/46* (2013.01)
USPC ........................................ 423/445 R; 423/650

(58) Field of Classification Search
CPC ................................................... Y02E 50/00
See application file for complete search history.

(56) References Cited

U.S. PATENT DOCUMENTS 2,208,157 A   7/1940 Fritz
2,398,828 A   4/1946 Gray
3,888,896 A * 6/1975 Espino et al. ................. 518/700

(Continued)

FOREIGN PATENT DOCUMENTS

CN    101306302 A    11/2008
EP    0485922 A1 *  11/1991

(Continued)

OTHER PUBLICATIONS

Turner, John A., A Realizable Renewable Energy Future, Science, vol. 285, 1999, pp. 687-689.*

(Continued)

*Primary Examiner* — Harry D Wilkins, III
(74) *Attorney, Agent, or Firm* — Perkins Coie LLP

(57) ABSTRACT

The present disclosure is directed to a system and method of sustainable economic development, such as development through an integrated production of renewable energy, material resources, and nutrient regimes. In some embodiments, the system utilizes resources extracted from renewable energy sources to assist in the capture of energy from other renewable energy sources. In some embodiments, the system utilizes energy from renewable energy sources to extract resources from other renewable energy sources.

34 Claims, 15 Drawing Sheets

(56) References Cited

U.S. PATENT DOCUMENTS

| | | | | |
|---|---|---|---|---|
| 4,105,755 | A | 8/1978 | Darnell et al. | |
| 4,124,481 | A | 11/1978 | Ramer | |
| 4,172,506 | A | 10/1979 | Terry | |
| 4,200,505 | A | 4/1980 | Day et al. | |
| 4,319,635 | A * | 3/1982 | Jones | 166/401 |
| 4,341,607 | A * | 7/1982 | Tison | 205/343 |
| 4,341,608 | A * | 7/1982 | St. John | 205/639 |
| 4,382,189 | A | 5/1983 | Wilson | |
| 4,386,801 | A | 6/1983 | Chapman et al. | |
| 4,389,288 | A | 6/1983 | Vaughan | |
| 4,395,316 | A | 7/1983 | St. John | |
| 4,437,954 | A * | 3/1984 | Sammells et al. | 205/340 |
| 4,455,045 | A | 6/1984 | Wheeler | |
| 4,468,235 | A | 8/1984 | Hill | |
| 4,601,508 | A | 7/1986 | Kerian | |
| 4,611,847 | A | 9/1986 | Sullivan | |
| 4,620,900 | A | 11/1986 | Kimura et al. | |
| 4,736,111 | A | 4/1988 | Linden | |
| 4,746,160 | A | 5/1988 | Wiesemeyer | |
| 4,896,507 | A * | 1/1990 | Hosford | 60/641.8 |
| 4,902,307 | A | 2/1990 | Gavalas et al. | |
| 4,978,162 | A | 12/1990 | Labbe | |
| 4,985,055 | A | 1/1991 | Thorne et al. | |
| 5,024,818 | A * | 6/1991 | Tibbetts et al. | 422/158 |
| 5,026,403 | A * | 6/1991 | Michel-Kim | 48/203 |
| 5,058,945 | A | 10/1991 | Elliott, Sr. et al. | |
| 5,119,897 | A | 6/1992 | Moriwake | |
| 5,132,007 | A * | 7/1992 | Meyer et al. | 208/427 |
| 5,222,698 | A | 6/1993 | Nelson et al. | |
| 5,259,870 | A | 11/1993 | Edlund | |
| 5,280,990 | A | 1/1994 | Rinard | |
| 5,323,061 | A | 6/1994 | Immler et al. | |
| 5,343,699 | A | 9/1994 | McAlister | |
| 5,407,245 | A | 4/1995 | Geropp | |
| 5,417,817 | A * | 5/1995 | Dammann et al. | 205/335 |
| 5,498,059 | A | 3/1996 | Switlik | |
| 5,560,443 | A | 10/1996 | DuBose | |
| 5,617,504 | A | 4/1997 | Sciacca et al. | |
| 5,662,389 | A | 9/1997 | Truglio et al. | |
| 5,719,990 | A | 2/1998 | Yang | |
| 5,806,553 | A | 9/1998 | Sidwell | |
| 5,986,429 | A | 11/1999 | Mula, Jr. | |
| 6,015,065 | A | 1/2000 | McAlister | |
| 6,068,328 | A | 5/2000 | Gazdzinski | |
| 6,081,183 | A | 6/2000 | Mading et al. | |
| 6,083,377 | A | 7/2000 | Lin et al. | |
| 6,090,266 | A * | 7/2000 | Roychowdhury | 205/637 |
| 6,092,861 | A | 7/2000 | Whelan | |
| 6,155,212 | A | 12/2000 | McAlister | |
| 6,200,069 | B1 | 3/2001 | Miller | |
| 6,216,599 | B1 | 4/2001 | Cavanagh | |
| 6,220,193 | B1 | 4/2001 | Dilks | |
| 6,309,010 | B1 | 10/2001 | Whitten | |
| 6,378,932 | B1 | 4/2002 | Fasel et al. | |
| 6,402,810 | B1 | 6/2002 | Mayer et al. | |
| 6,409,252 | B1 | 6/2002 | Andrus | |
| 6,446,597 | B1 | 9/2002 | McAlister | |
| 6,468,684 | B1 | 10/2002 | Chisholm et al. | |
| 6,500,313 | B2 * | 12/2002 | Sherwood | 204/157.15 |
| 6,502,533 | B1 | 1/2003 | Meacham | |
| 6,503,584 | B1 | 1/2003 | McAlister | |
| 6,516,754 | B2 | 2/2003 | Chadwick | |
| 6,525,431 | B1 | 2/2003 | Clucas et al. | |
| 6,606,860 | B2 | 8/2003 | McFarland | |
| 6,749,043 | B2 | 6/2004 | Brown et al. | |
| 6,755,899 | B2 | 6/2004 | Nagai | |
| 6,756,140 | B1 | 6/2004 | McAlister | |
| 6,757,591 | B2 | 6/2004 | Kramer | |
| 6,784,562 | B2 | 8/2004 | Gennesseaux | |
| 6,838,782 | B2 | 1/2005 | Vu | |
| 6,854,788 | B1 | 2/2005 | Graham | |
| 6,897,575 | B1 | 5/2005 | Yu | |
| 6,926,345 | B2 | 8/2005 | Ortega et al. | |
| 6,979,049 | B2 | 12/2005 | Ortega et al. | |
| 6,984,305 | B2 | 1/2006 | McAlister | |
| 7,033,570 | B2 * | 4/2006 | Weimer et al. | 423/650 |
| 7,062,913 | B2 | 6/2006 | Christensen et al. | |
| 7,152,908 | B2 | 12/2006 | Shahbazi | |
| 7,165,804 | B2 | 1/2007 | Shahbazi | |
| 7,185,944 | B2 | 3/2007 | Shahbazi | |
| 7,207,620 | B2 | 4/2007 | Cosgrove et al. | |
| 7,210,467 | B2 | 5/2007 | Kweon et al. | |
| 7,211,905 | B1 | 5/2007 | McDavid, Jr. | |
| 7,237,827 | B2 | 7/2007 | Shahbazi | |
| 7,243,980 | B2 | 7/2007 | Vala | |
| 7,254,944 | B1 | 8/2007 | Goetzinger et al. | |
| 7,364,810 | B2 | 4/2008 | Sridhar et al. | |
| 7,427,189 | B2 * | 9/2008 | Eyb | 416/226 |
| 7,592,383 | B2 | 9/2009 | Fukui | |
| 7,632,338 | B2 | 12/2009 | Cipollini | |
| 7,797,183 | B2 | 9/2010 | Dias et al. | |
| 7,827,974 | B2 | 11/2010 | Beckmann | |
| 7,931,784 | B2 * | 4/2011 | Medoff | 204/157.63 |
| 8,165,968 | B2 | 4/2012 | Ramesh et al. | |
| 8,187,549 | B2 * | 5/2012 | McAlister | 422/186 |
| 8,187,550 | B2 * | 5/2012 | McAlister | 422/186 |
| 8,285,635 | B2 | 10/2012 | Rhodes, III | |
| 8,313,556 | B2 | 11/2012 | McAlister | |
| 8,595,020 | B2 | 11/2013 | Marino | |
| 2001/0035093 | A1 | 11/2001 | Yokota | |
| 2002/0007845 | A1* | 1/2002 | Collette et al. | 136/246 |
| 2003/0012985 | A1 | 1/2003 | McAlister | |
| 2003/0018487 | A1 | 1/2003 | Young et al. | |
| 2003/0039608 | A1 | 2/2003 | Shah et al. | |
| 2003/0062270 | A1* | 4/2003 | McAlister | 205/697 |
| 2004/0089439 | A1 | 5/2004 | Treverton et al. | |
| 2004/0124095 | A1 | 7/2004 | Fujimura et al. | |
| 2004/0126632 | A1 | 7/2004 | Pearson | |
| 2005/0003247 | A1 | 1/2005 | Pham | |
| 2005/0015287 | A1 | 1/2005 | Beaver | |
| 2005/0109394 | A1 | 5/2005 | Anderson | |
| 2006/0005738 | A1 | 1/2006 | Kumar | |
| 2006/0005739 | A1 | 1/2006 | Kumar | |
| 2006/0048770 | A1* | 3/2006 | Meksvanh et al. | 126/620 |
| 2006/0049063 | A1* | 3/2006 | Murphy et al. | 205/552 |
| 2006/0100897 | A1 | 5/2006 | Halloran et al. | |
| 2006/0162554 | A1 | 7/2006 | Kelley | |
| 2006/0257310 | A1* | 11/2006 | Tada et al. | 423/447.3 |
| 2006/0286518 | A1 | 12/2006 | Yoder | |
| 2007/0138006 | A1 | 6/2007 | Oakes et al. | |
| 2007/0220887 | A1 | 9/2007 | Monostory et al. | |
| 2008/0050800 | A1* | 2/2008 | McKeeman et al. | 435/262.5 |
| 2008/0078675 | A1 | 4/2008 | Kawahara et al. | |
| 2008/0088135 | A1* | 4/2008 | Novo Vidal | 290/54 |
| 2008/0102329 | A1 | 5/2008 | Hollinger | |
| 2008/0115415 | A1* | 5/2008 | Agrawal et al. | 48/101 |
| 2008/0138675 | A1 | 6/2008 | Jang et al. | |
| 2008/0245672 | A1 | 10/2008 | Little et al. | |
| 2008/0303348 | A1 | 12/2008 | Witters | |
| 2008/0318092 | A1 | 12/2008 | Sridhar et al. | |
| 2009/0016948 | A1* | 1/2009 | Young | 423/414 |
| 2009/0169452 | A1* | 7/2009 | Constantz et al. | 423/230 |
| 2009/0215137 | A1 | 8/2009 | Hawkins et al. | |
| 2009/0217584 | A1* | 9/2009 | Raman et al. | 48/127.7 |
| 2009/0222307 | A1 | 9/2009 | Beaver | |
| 2009/0235587 | A1 | 9/2009 | Hawkes et al. | |
| 2009/0263540 | A1* | 10/2009 | Allen et al. | 426/11 |
| 2009/0266075 | A1* | 10/2009 | Westmeier et al. | 60/651 |
| 2009/0276265 | A1 | 11/2009 | Ahmed et al. | |
| 2010/0101231 | A1* | 4/2010 | Westmeier | 60/783 |
| 2010/0107994 | A1 | 5/2010 | Moriarty et al. | |
| 2010/0306002 | A1 | 12/2010 | Dias et al. | |
| 2011/0041784 | A1 | 2/2011 | McAlister | |
| 2011/0070510 | A1 | 3/2011 | McAlister | |
| 2011/0081586 | A1 | 4/2011 | McAlister | |
| 2011/0198211 | A1* | 8/2011 | McAlister | 204/157.46 |
| 2011/0200897 | A1 | 8/2011 | McAlister | |
| 2011/0230573 | A1* | 9/2011 | McAlister | 518/702 |

(56) References Cited

U.S. PATENT DOCUMENTS

| | | | |
|---|---|---|---|
| 2012/0271677 | A1 | 10/2012 | Rhodes, III |
| 2012/0323619 | A1 | 12/2012 | Risz et al. |

FOREIGN PATENT DOCUMENTS

| | | | |
|---|---|---|---|
| EP | 2103682 | | 9/2009 |
| EP | 2103682 A1 | * | 9/2009 |
| GB | 2 248 230 A | | 1/1992 |
| GB | 2 248 230 A | * | 4/1992 |
| JP | 04-076211 | | 3/1992 |
| JP | 04-357969 A | | 12/1992 |
| JP | 05-223268 | | 8/1993 |
| JP | 07-113567 | | 5/1995 |
| JP | 2000-205044 | | 7/2000 |
| JP | 2000-297700 | | 10/2000 |
| JP | 2002-119822 A | | 4/2002 |
| JP | 2005200252 A | | 7/2005 |
| JP | 2006-128006 | | 5/2006 |
| KR | 10-0808736 | | 2/2008 |
| KR | 10-090119098 | | 11/2009 |
| WO | WO-01-56938 | | 8/2001 |
| WO | WO-2006119118 A2 | | 11/2006 |
| WO | WO-2006-136860 | | 12/2006 |
| WO | WO-2008-115933 | | 9/2008 |

OTHER PUBLICATIONS

Muradov et al, From hydrocarbon to hydrogen-carbon to hydrogen economy, Internation Journal of Hydrogen Energy, vol. 30, 2005, pp. 225-237.*

Koinuma et al, Sahara Solar Breeder Foundation official website, archived copy from Feb. 2011, http://www.ssb-foundation.com/obtained via www.archive.org.*

G8-5 Academies' Meeting, Rome, Mar. 2009.*

Milne et al, "Hydrogen from Biomass", NREL, 2002.*

Muradov et al, ""Green" path from fossil-based to hydrogen economy: An overview of carbon-neutral technologies", Internation Journal of Hydrogen Energy, vol. 33, Issue 23, Dec. 2008, pp. 6804-6839.*

Lindmayer et al, "Solar Breeder: Energy Payback Time for Silicon Photovoltaic Systems", Apr. 1977.*

"Features." Accessed: Aug. 12, 2010. <http://www.pre.nl/simapro/simapro_lca_software.htm>. pp. 1-7.

"GaBi Software: Results and Interpretation." Accessed: Aug. 12, 2010. <http://www.gabi-software.com/software/gabi-4/results-and-interpretation/>. p. 1.

California Clean Air Conversions, LLC. Advanced Green Innovations, LLC. "Meeting California's 2010 Vision: Renewable Hydrogen Production and Fleet Conversion" 2010. p. 1.

Fernando, Vincent. "Exxon: Here's Why We Just Spent $41 Billlion on Natural Gas." Business Insider. Published: Dec. 14, 2009. Web. <http://www.businessinsider.com/exxon-heres-why-we-just-spent-41-billion-on-natural-gas-2009-12>. pp. 1-8.

Holdren, John P. "Meeting the Climate-Change Challenge." Lecture Slides. The John H. Chafee Memorial Lecture. Washington DC. Jan. 17, 2008. pp. 1-52.

International Maritime Organization. "Prevention of Air Pollution from Ships." Marine Environment Protection Committee. 59th Session, Agenda Item 4. Apr. 9, 2009. pp. 1-289.

International Search Report and Written Opinion for Application No. PCT/US2010/002260; Applicant: McAlister Technologies, LLC.; Date of Mailing: Apr. 28, 2011. pp. 1-8.

International Search Report and Written Opinion for Application No. PCT/US2010/045664; Applicant: McAlister Technologies, LLC.; Date of Mailing: Apr. 15, 2011. pp. 1-8.

International Search Report and Written Opinion for Application No. PCT/US2010/045674; Applicant: McAlister Technologies, LLC.; Date of Mailing: Apr. 29, 2011. pp. 1-9.

McAlister, Roy. "Maximizing Renewable Energy Efficiencies: A Full Spectrum Approach." Feb. 2009. pp. 1-21.

McAlister, Roy. "Sustainable Hydrogen Hyway." California Clean Air Conversions, LLC. Advanced Green Innovations, LLC. 2010. pp. 1-6.

Murray, Don. "World Energy Park." Starpoint Solar. Presentation. Accessed: Jun. 4, 2009. pp. 1-33.

First Action Interview Office Action for U.S. Appl. No. 13/027,235; Applicant: McAlister Technologies, LLC.; Date of Mailing: Oct. 20, 2011. pp. 1-4.

Non-Final Office Action for U.S. Appl. No. 12/857,554; Applicant: McAlister Technologies, LLC.; Date of Mailing: Nov. 21, 2011. pp. 1-30.

International Search Report and Written Opinion for Application No. PCT/US11/024813; Applicant: McAlister Technologies, LLC; Date of Mailing: Nov. 30, 2011. pp. 1-12.

Zhang et al., "Economic Modelling Approaches to Cost Estimates for the Control of Carbon Dioxide Emissions," Energy Economics, 1998, vol. 20, pp. 101-120.

European Search Report for Application EP10814158.1; Date of Mailing Jan. 9, 2014; 11 pages.

Environmental Input-Output Assessment of Integrated Second Generation Biofuel Production in Fenno-Scandinavia, Jul. 2009.

Environmentally Smart Accounting Using Total Cost Assessment to advance Pollution Prevention, http://infohouse.p2ric.org/ref/31/30606.pdf, 1993.

Full Cost Accounting; "A Course Module on Incorporating Environmental and Social Costs into Traditional Business Accounting Systems," http://gdi.ce.cmu.edu/gd/education/FCA_Module_98.pdf.

Management's Discussion and Analysis—Yamana Gold for the Year Ended Dec. 31, 2009, http://www.yamana.com/Theme/Yamana/files/Yamana%20Gold%20Inc%202009%20MD&A%20and%20FS.pdf, Mar. 2010.

Repurposing Equipment; Cutting Costs, http://www.businessknowledgesource.com/manufacturing/repurposing_equipment_cutting_costs_028706.html, Jan. 2010.

\* cited by examiner

Full Spectrum Functional Zones; Embodiments

SUSTAINABLE ECONOMIC DEVELOPMENT THROUGH INTEGRATED PRODUCTION OF RENEWABLE ENERGY, MATERIALS RESOURCES, AND NUTRIENT REGIMES

CROSS-REFERENCE TO RELATED APPLICATION(S)

The present application claims priority to and the benefit of U.S. Provisional Patent Application No. 61/345,053 filed on May 14, 2010 and titled SYSTEM AND FOR RENEWABLE RESOURCE PRODUCTION and U.S. Provisional Application No. 61/304,403, filed Feb. 13, 2010 and titled FULL SPECTRUM ENERGY AND RESOURCE INDEPENDENCE. The present application is a continuation-in-part of each of the following applications: U.S. patent application Ser. No. 12/707,651, filed Feb. 17, 2010 and titled ELECTROLYTIC CELL AND METHOD OF USE THEREOF, now U.S. Pat. No. 8,075,748, issued Dec. 13, 2011; PCT Application No. PCT/US10/24497, filed Feb. 17, 2010 and titled ELECTROLYTIC CELL AND METHOD OF USE THEREOF, now published as WO 2010/096503 on Aug. 26, 2010; U.S. patent application Ser. No. 12/707,653, filed Feb. 17, 2010 and titled APPARATUS AND METHOD FOR CONTROLLING NUCLEATION DURING ELECTROLYSIS, now U.S. Pat. No. 8,172,990, issued May 8, 2012; PCT Application No. PCT/US10/24498, filed Feb. 17, 2010 and titled APPARATUS AND METHOD FOR CONTROLLING NUCLEATION DURING ELECTROLYSIS, now published as WO 2010/096504 on Aug. 26, 2010; U.S. patent application Ser. No. 12/707,656, filed Feb. 17, 2010 and titled APPARATUS AND METHOD FOR GAS CAPTURE DURING ELECTROLYSIS, now U.S. Pat. No. 8,075,749, issued Dec. 13, 2011; and PCT Application No. PCT/US10/24499, filed Feb. 17, 2010 and titled APPARATUS AND METHOD FOR CONTROLLING NUCLEATION DURING ELECTROLYSIS, now published as WO 2010/096505 on Aug. 26, 2010; each of which claims priority to and the benefit of the following applications: U.S. Provisional Patent Application No. 61/153,253, filed Feb. 17, 2009 and titled FULL SPECTRUM ENERGY; U.S. Provisional Patent Application No. 61/237,476, filed Aug. 27, 2009 and titled ELECTROLYZER AND ENERGY INDEPENDENCE TECHNOLOGIES; U.S. Provisional Application No. 61/304,403, filed Feb. 13, 2010 and titled FULL SPECTRUM ENERGY AND RESOURCE INDEPENDENCE. Each of these applications is incorporated by reference in its entirety.

BACKGROUND

Renewable energy sources such as solar, wind, wave, falling water, and biomass wastes have tremendous potential as being main energy sources, but currently suffer from a variety of problems that prohibit their widespread adoption. For example, utilizing renewable energy sources in the production of electricity is dependent on the availability of the sources, which can be intermittent. Solar energy is limited by the sun's availability (i.e., daytime only), wind energy is limited by the variability of wind, falling water energy is limited by droughts, and biomass is limited by seasonal variances, among other things. Because of these and other factors, much of the energy from renewable sources, captured or not captured, tends to be wasted.

These inefficiencies in capturing and saving energy limit the growth of renewable energy sources into viable energy providers for many regions of the world, because they often lead to high costs of producing energy using the renewable energy sources. Thus, the world continues to rely on oil and other fossil fuels as major energy sources because of more than a century of government subsidization for infrastructure and technology developments that make it deceptively convenient and seemingly inexpensive for the present generation to expend fossil reserves for production of usable energy. Exploitation of finite fossil and fissionable fuel reserves provides a false sense of value because the replacement cost for the resource expended and the cost of environmental degradation along with the health impacts that are incurred are not included in the purchase price for such energy.

Surplus electricity, particularly power from large coal- and nuclear-fueled central power plants presents hidden costs including related environmental pollution problems of prompt production of toxic emissions of heavy metal residues and greenhouse gases from fossil fuel combustion along with requirements for expensive long-term storage of radioactive wastes. Large expenses for capital equipment, maintenance, and fuel costs to provide sufficient capacity to meet customer demands are incurred in present utility power distribution systems.

These and other problems exist with respect to the sustainable production and utilization of renewable resources.

DETAILED DESCRIPTION

Cross-Reference to Related Applications

Figure 1A:
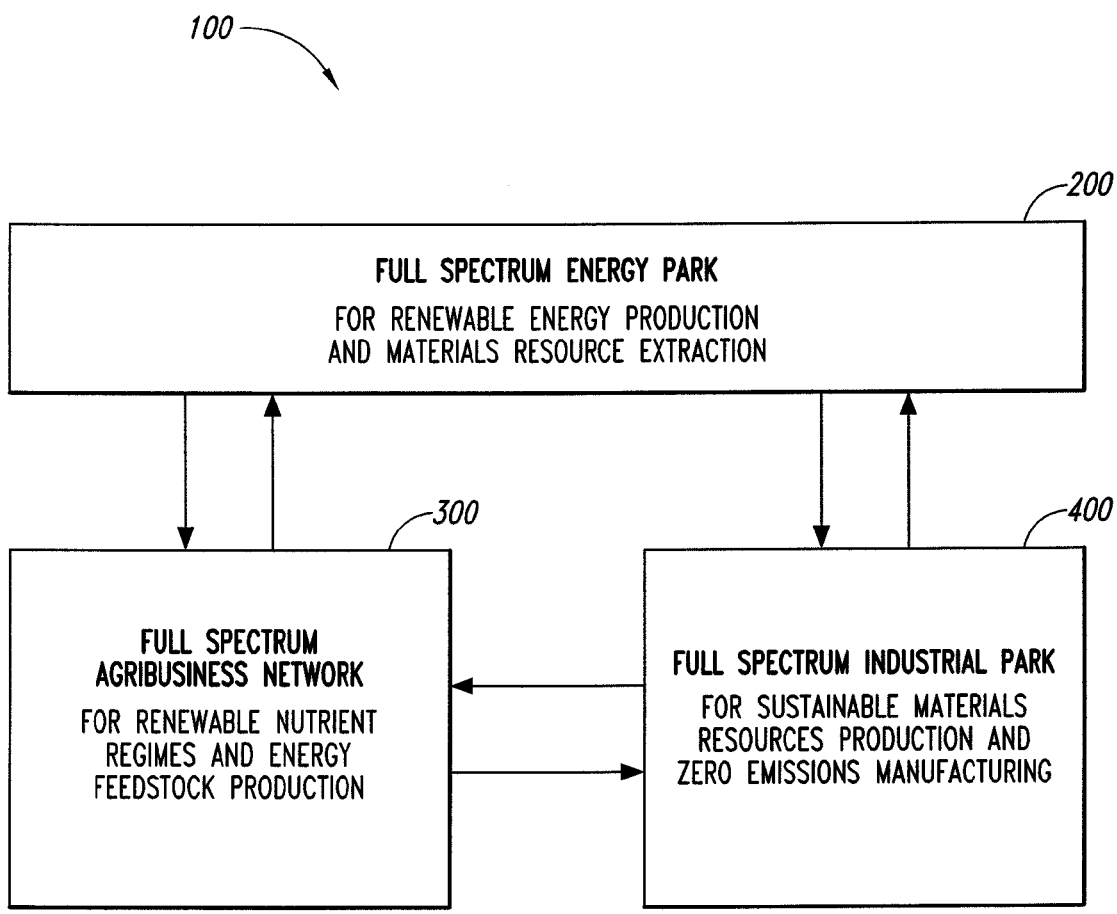
FIG. 1A is a block diagram illustrating a system of integrated energy, agribusiness and industrial sustainable economic development in accordance with aspects of the disclosure.

The present application incorporates by reference in its entirety the subject matter of U.S. Provisional Patent Application No. 60/626,021, filed Nov. 9, 2004 and titled MULTI-FUEL STORAGE, METERING AND IGNITION SYSTEM. The present application incorporates by reference in their entirety the subject matter of each of the following U.S. Patent Applications, filed concurrently herewith on Aug. 16, 2010: U.S. patent application Ser. No. 12/806,634, titled METHODS AND APPARATUSES FOR DETECTION OF PROPERTIES OF FLUID CONVEYANCE SYSTEMS; U.S. Provisional Application No. 61/401,699 titled COMPREHENSIVE COST MODELING OF AUTOGENOUS SYSTEMS AND PROCESSES FOR THE PRODUCTION OF ENERGY, MATERIAL RESOURCES AND NUTRIENT REGIMES; U.S. application Ser. No. 12/806,633 titled ELECTROLYTIC CELL AND METHOD OF USE THEREOF; U.S. application Ser. No. 12/857,541 titled SYSTEMS AND METHODS FOR SUSTAINABLE ECONOMIC DEVELOPMENT THROUGH INTEGRATED FULL SPECTRUM PRODUCTION OF RENEWABLE ENERGY; U.S. application Ser. No. 12/857,554 titled SUSTAINABLE ECONOMIC DEVELOPMENT THROUGH INTEGRATED FULL SPECTRUM PRODUCTION OF RENEWABLE MATERIAL RESOURCES; U.S. application Ser. No. 12/857,546 titled METHOD AND SYSTEM FOR INCREASING THE EFFICIENCY OF SUPPLEMENTED OCEAN THERMAL ENERGY CONVERSION (SOTEC); U.S. application Ser. No. 12/857,228 titled GAS HYDRATE CONVERSION SYSTEM FOR HARVESTING HYDROCARBON HYDRATE DEPOSITS; U.S. application Ser. No. 12/857,515 entitled APPARATUSES AND METHODS FOR STORING AND/OR FILTERING A SUBSTANCE; U.S. application Ser. No. 12/857,502 titled ENERGY SYSTEM FOR DWELLING SUPPORT; U.S. application Ser. No. 12/857,433 titled ENERGY CONVERSION ASSEMBLIES AND ASSOCIATED METHODS OF USE AND MANUFACTURE; and U.S. application Ser. No. 12/857,461 titled INTERNALLY REINFORCED STRUCTURAL COMPOSITES AND ASSOCIATED METHODS OF MANUFACTURING.

Overview

A system for applying renewable energy to feedstock and other inputs to achieve refined renewable energy and, thus, economic sustainability with respect to the production of resources from the feedstock, is described. Surplus electricity, particularly power from large coal and nuclear-fueled central power plants presents another economic problem and opportunity that is largely wasted but the present invention provides for utilization of such surplus capacity for creation of renewable energy, materials, and nutrients. This solution provides improvements in the returns on present investments and establishes incentives for transition to sustainable economic development practices. Illustratively surplus electricity from fossil or nuclear fueled power plants may be utilized interchangeably with renewable electricity to produce carbon reinforcement materials for solar dish-gensets along with wind and water turbines in which such reinforcing carbon is extracted from hydrocarbons such as methane from sources including renewable and fossil sources. The on-going production of renewable electricity from such solar dish-gensets and turbines for harnessing wind and moving water is typically many times larger than the one-time combustion of such hydrocarbons and capacity to efficiently meet customer demands is greatly improved.

During production of a resource (e.g. hydrogen, oxygen, carbon), the system utilizes a renewable process that captures and reinvests into the system some or all resources and/or byproducts from the extraction of the resource using renewable energy. In some embodiments, the system enables the sustainable production of hydrogen, carbon, and other resources. In some embodiments, the system harnesses energy during and as a result of the sustainable production of resources. In some embodiments, the system provides for sustainable economic development by refining renewable energy input into the system and, therefore, achieving economic multiplying effects on feedstock, resources, and other substances within the system.

Many of the details, dimensions, angles, shapes, and other features shown in the Figures are merely illustrative of particular embodiments of the disclosure. Accordingly, other embodiments can have other details, dimensions, angles, and features without departing from the spirit or scope of the present disclosure. In addition, those of ordinary skill in the art will appreciate that further embodiments of the disclosure can be practiced without several of the details described below.

Reference throughout this specification to "one embodiment" or "an embodiment" means that a particular feature, structure, or characteristic described in connection with the embodiment is included in at least one embodiment of the present disclosure. Thus, the occurrences of the phrases "in one embodiment" or "in an embodiment" in various places throughout this Specification are not necessarily all referring to the same embodiment. Furthermore, the particular features, structures, or characteristics may be combined in any suitable manner in one or more embodiments. In addition, the headings provided herein are for convenience only and do not interpret the scope or meaning of the claimed disclosure.

The Overall System

FIG. 1A shows the Full Spectrum Integrated Production System 100, composed of three interrelated systems, that include The Full Spectrum Energy Park 200 for Renewable Energy Production and Materials Resource Extraction, The Full Spectrum Agribusiness Network 300 for Renewable Nutrient Regimes (human, animal and plant nutrition) and Energy Feedstock Production (biomass, biowaste and biofuel), and Full Spectrum Industrial Park 400 for Sustainable Materials Resource Production and Zero Emissions Manufacturing.

FIG. 1A shows system 100 as the integration of systems 200, 300, and 400 to enable exchange of energy, materials and information among these systems. System 100 integration, and particularly methods within system 200, utilizes the thermodynamic properties of multiple interrelated heat engines thermally coupled to form a thermodynamic whole-system in order to function effectively as a very large heat engine, which is able to achieve increased beneficial production capacity and efficiency. Within system 100, system 200 is particularly dedicated to achieve synergistic linkage among solar thermal, geothermal, ocean thermal, and engine thermal sources so as to increase the total available renewable energy output of the particular site location, and to provide energy and extracted material resources to systems 300 and 400.

The Full Spectrum Energy Park 200 is thermally coupled to function effectively as a single large heat engine, whose systems and subsystems are interrelated to establish energy cascades, using working fluids that are heated in two or more stages. The total available renewable energy output of system 200 is increased by systematically moving working fluids between solar, geologic, engine, and other thermal sources to achieve a cascade effect to optimize the thermodynamic properties (such as temperature, pressure, purity, phase shift, and efficiency of energy conversion) of a working fluid. Energy output of one stage is re-invested in key processes of another stage so as to operate in a regenerative or autogenous manner with increased efficiency and economy of operation.

Full Spectrum Energy Park 200 functions include: harvesting, conversion and storage of kinetic, thermal, and radiant energy forms among renewable energy sources such as solar, wind, moving water, geothermal, biomass, and internal combustion engines so as to establish autogenous or regenerative energy cascades among the systems to create aggregating and synergistic benefits that cannot be achieved by harvesting, conversion and storage of any one renewal energy source alone. Autogenous or regenerative energy methods are practiced in systems 200, 300, and 400. Further, system 200 is directed to materials resource extraction of numerous chemicals for use in systems 300 and 400. For example, thermochemical regeneration is used as a means of extracting carbon as a raw material (extraction can take place in systems 200, 300 and 400) for subsequent manufacturing production of durable goods at system 400. In another example, thermochemical regeneration can also be used as a means of extracting nitrogen and trace minerals for subsequent manufacturing production of plant fertilizers for use in system 300. Further, system 200 is directed to biowaste, biomass and biofuel conversion, typically to achieve bio-methane gas and/or hydrogen gas storage, transport and use on-demand at systems 200, 300 and 400 as fuels for internal combustion engines and/or fuel cells for electrical power generation and/or transportation.

The manipulation of solar thermal, geothermal, ocean thermal, and engine thermal sources provides a highly adaptive integrated platform for installations of system 100 at various climate regions of location, and installations that are both land-based and ocean-based. Engineering for increased location adaptability thereby significantly increases the total availability of renewable energy harvesting, and thus provides an economically viable solution for local, regional, national and global economies.

Food production at system 300 can be installed on both land and ocean sites. Crop farms, cattle farms, ranches, industrial production facilities for pork and chicken, fresh water fisheries, ocean fisheries, dairy farms, and so on can be linked to system 200 as consumers of the energy produced in system 200, but in turn produce waste by-products which are diverted to system 200 for conversion to renewable energy and renewable materials resources. Further, system 300 is directed to increased Energy Feedstock Production for such biofuel crops, such as algae, switch grass and other crops to increase the viability of photosynthesis-based energy harvesting. Method and apparatus for water production, purification, and conservation are used in each of the systems of production 200, 300 and 400. However, these are important components of system 300 in order to satisfy requirements for large quantities of water in food production and to overcome the documented problem of unsustainability due to waste and fouling of water by conventional food production practices.

System integration increases capacity for "sustainability"—defined as increased production of energy, material resources and nutrient regimes using renewable methods to avoid depletion of natural resources and reduce or eliminate destructive environmental impact such as pollution and toxic emissions as by-products of production. Sustainability requires methods of production for energy, materials, and food that are viable for the long-term wellbeing of future generations, not just the immediate short-term benefit of current consumers.

System integration enables the increase in production capacity for "economic scalability"—defined as significant increase of production of energy, materials, and food that is achieved by the ability to replicate numerous aggregative installation sites, and to increase the number of available site locations by greatly improved adaptability to the diverse climate regions (i.e., adaptively harvesting renewable energy by accommodating the varied resource characteristics of temperate, tropical and arctic climates). Such economic scalability is required to increase the earth's carrying capacity to sustain continued rapid human population growth, and rapidly increasing energy requirements of developing nations. For successful use, such production methods and locations must be immediately usable, and must present an economically viable alternative to current production means of energy, materials, and food production as compared to using conventional fossil fuel and/or nuclear energy sources.

System integration further enables a zero-emissions and zero-waste method of energy production 200, materials production 400, and food production 300, wherein: organic waste generated in the system 300 that would otherwise be burned, buried, or dumped in landfills, aquifers, streams, oceans, or emitted into the atmosphere as pollutants is instead systematically channeled into biomass, biowaste, and biofuel conversion systems as found in system 200; energy and material resource extraction in system 200 is passed to system 400 for production of durable goods; energy and material resource extraction in system 200 is also passed to system 300 for production of nutrient regimes for humans, animals and plant life on land and ocean.

System integration establishes a single unit of economic production that intentionally links energy production with food production and materials resource production in such a way that these function as an interdependent whole.

The Full Spectrum Integrated Production System is thus suitable for installation in locations or communities where no comparable renewable energy infrastructure currently exists, or where manufacturing capabilities are deficient and unemployment is the norm, or where food production is deficient and poverty and malnourishment is the norm. The goal of introducing this unified method of economic production is to enable increases in gross domestic product (GDP) with the increased quality of life that accompanies GDP, and systematic job creation with the improved quality of life that accompanies meaningful employment.

Furthermore, system integration establishes a single unit of economic production that intentionally links waste management with energy conversion practices so that they function as an interdependent whole to interrupt conventional waste practices of burn, bury, and dump that lead to pollution and environmental degradation.

The Full Spectrum Integrated Production System introduces use of sustainable waste-to-energy conversion as an integrated practice across the whole system. The goal of this integrated system is to protect the natural environment, conserve finite natural resources, reduce communicable disease, and reduce land, water and air pollution (including reduction in greenhouse gas drivers of climate change, such as methane and $CO_2$).

The Full Spectrum Integrated Production System 100 provides a means to achieve an "industrial ecology," in which the human-systems production environment mimics natural eco-systems: where energy and materials flow among systems and wastes become inputs for new processes in a closed-loop manner, yet the whole system is open to the renewable, sustainable energy provided by sun (solar thermal), earth (geothermal), ocean (ocean thermal), and biomass conversion (engine thermal) systems.

Figure 1B:
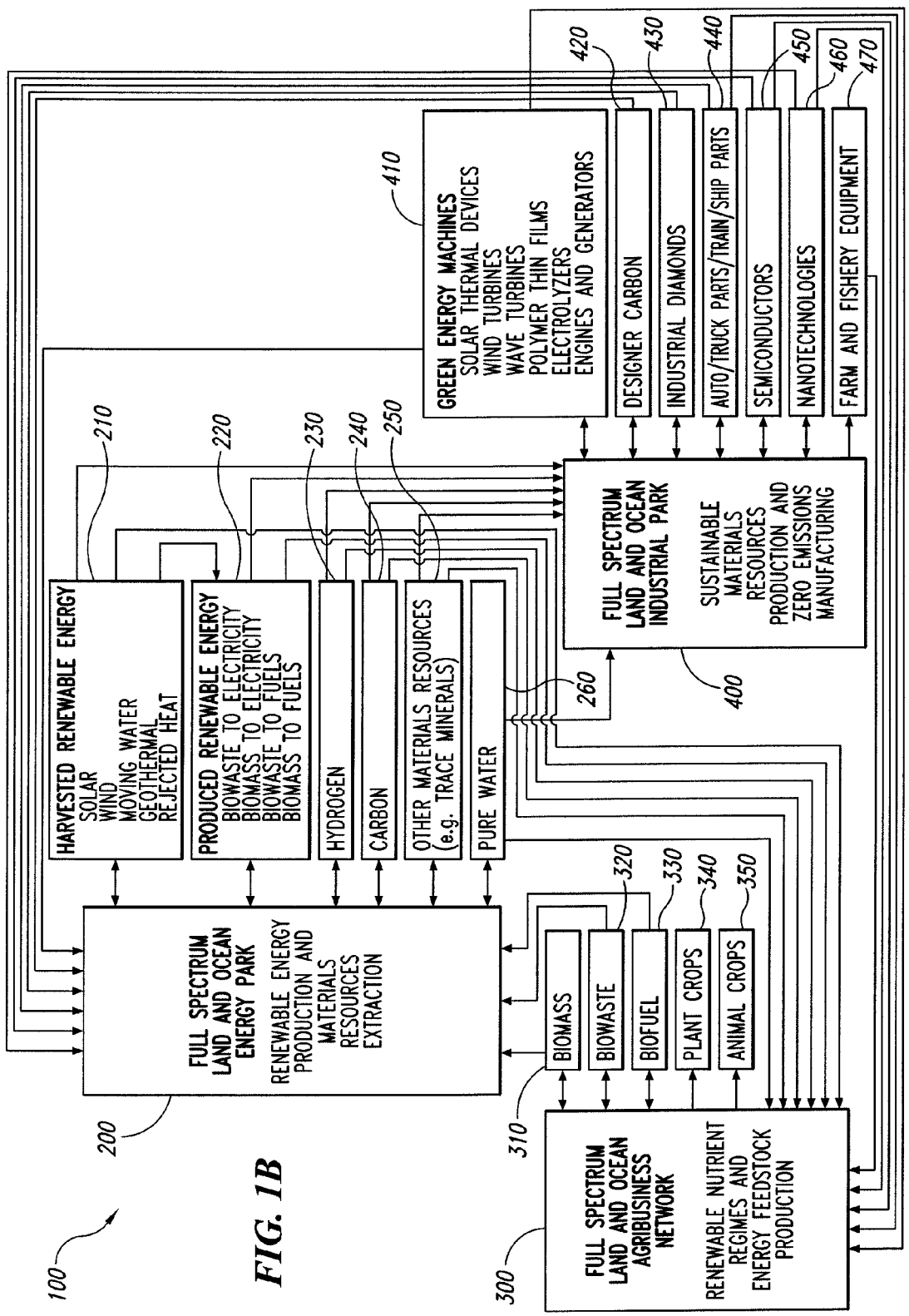
FIG. 1B is a block diagram illustrating a system of integrated production of sustainable economic development in accordance with aspects of the disclosure.

FIG. 1B is a block diagram illustrating a Full Spectrum Integrated Production System 100 of sustainable economic development, which includes the production of energy (e.g., electricity and fuels) concurrent with the production of nutrient regimes (e.g., products for human, animal, or plant nutrition) and the production of materials resources (e.g., hydrogen and carbon). The system 100 is comprised of integrated and interdependent sub-systems with adaptive control of autogenous cascading energy conversions that captures and reinvests some or all of the energy, substances and/or byproducts of each sub-system. Thus, the continued operation of the system 100 is sustained with the introduction of minimal or no external energy or materials resources. The system 100 is an example of industrial ecology which facilitates sustainable economic development, such as the harnessing of renewable energy, the production of foods, and the production of materials resources, which is greater production of energy, foods, and materials resources than is achievable using conventional techniques, among other benefits.

A Full Spectrum Energy Park 200 coordinates methods of capturing energy from renewable sources 210 (e.g., solar, wind, moving water, geothermal, rejected heat) with methods of producing energy from renewable feedstocks 220 (e.g., biowaste 320, biomass 310) and methods of producing materials resources (e.g., hydrogen 230, carbon 240, other materials resources such as trace minerals 250, pure water 260). Energy is stored, retrieved, and transported using methods of adaptive control of autogenous cascading energy conversions that generate a multiplier effect in the production of energy. During the energy harvesting and production processes, materials resources (e.g., hydrogen and carbon) are extracted from biowaste and biomass feedstocks used in the production of renewable energy. The Full Spectrum Energy Park 200 stores, retrieves, transports, monitors, and controls said energy and said resources to achieve improved efficiencies in the production of energy, materials resources, and nutrient regimes.

Some of the produced or harvested energy 210, 220 is provided to the Full Spectrum Agribusiness Network 300. Some of the produced energy 210, 220 is provided to the Full Spectrum Industrial Park 400. Some of the produced energy 210, 220 is reinvested in the Full Spectrum Energy Park 200. Some of the produced energy 201, 220 is provided to external recipients and/or added to the national electricity grid and/or the national gas pipeline.

A Full Spectrum Agribusiness Network 300 receives renewable energy produced by the Full Spectrum Energy Park 200 to power the functions of farming, animal husbandry, and fishery sub-systems. This includes renewable fuels for farm equipment, vehicles, boats and ships, and electricity for light, heat, mechanical equipment, and so on.

The Full Spectrum Agribusiness Network 300 receives materials resources and byproducts such as other materials resources (e.g., trace minerals 250) and pure water 260 produced by the Full Spectrum Energy Park 200 to enrich nutrient regimes in farming, animal husbandry, and fishery sub-systems and to produce increased efficiencies in the production of plant crops 340 and animal crops 350.

The Full Spectrum Agribusiness Network 300 harvests energy feedstock and supplies it to the Full Spectrum Energy Park 200 for use in the production of renewable energy. Suitable feedstock includes biomass 310 (e.g., crop slash), biowaste 320 (e.g., sewage, agricultural waste water, meat packing wastes, effluent from fisheries), biofuel stock 330 (e.g., algae, switchgrass), and so on.

A Full Spectrum Industrial Park 400 ruses renewable energy produced by the Full Spectrum Energy Park 200 to power the functions of sustainable materials resources production and zero-emissions manufacturing. This includes renewable fuels for internal combustion engines (e.g., stationary engines, vehicles) and electricity for light, heat, mechanical equipment, and so on.

The Full Spectrum Industrial Park 400 invests materials resources 230, 240 and byproducts 250 received from the Full Spectrum Energy Park 200 to produce additional materials resources (e.g., designer carbon 420 and industrial diamonds 430).

The Full Spectrum Industrial Park 400 uses materials resources and byproducts received from the Full Spectrum Energy Park 200 to manufacture products such as carbon-based green energy machines 410, including solar thermal devices 410, wind turbines 410, water turbines 410, electrolyzers 410, internal combustion engines and generators 410, automobile, ship and truck parts 440, semiconductors 450, nanotechnologies 460, farm and fishery equipment 470, and so on.

The Full Spectrum Industrial Park 400 provides some or all of these products and byproducts to the Full Spectrum Energy Park 200 and the Full Spectrum Agribusiness Network 300.

The Full Spectrum Energy Park 200 uses solar thermal devices 410, wind turbines 410, water turbines 410, electrolyzers 410, internal combustion engines and generators 410, and so on that are produced and provided by the Full Spectrum Industrial Park 400 to produce renewable energy.

The Full Spectrum Agribusiness Network 300 uses internal combustion engines and generators 410, farm and fishery equipment 470 and other devices produced and provided by the Full Spectrum Industrial Park 400 to produce nutrient regimes.

The energy produced by the Full Spectrum Integrated Production System 100 provides power for all the sub-systems, including reinvesting energy to drive the further production of renewable energy. Concurrently, some or all of the products and byproducts produced in the system 100 are invested in the functions of all the sub-systems. At the same time, the wastes produced by the system 100 are captured and used as feedstock for the functions of all the sub-systems. The integrated and interdependent sub-systems use adaptive controls to manage autogenous cascading energy conversions and autogenous regeneration of materials resources. Thus, the system constantly reinvests renewable energy, sustainable materials resources, and other byproducts into the different sources and processes of the sub-systems (Energy Park, Agribusiness Network, Industrial Park). In this manner, the system 100 harnesses larger amounts of the supplied energy and resource from various resources within the system than is achievable with conventional means. This industrial symbiosis generates a multiplying effect on the amounts of various resources and energy harvested from renewable feedstock and byproduct sources within the system, adding value, reducing costs, and improving the environment, among other benefits.

Figure 1C:
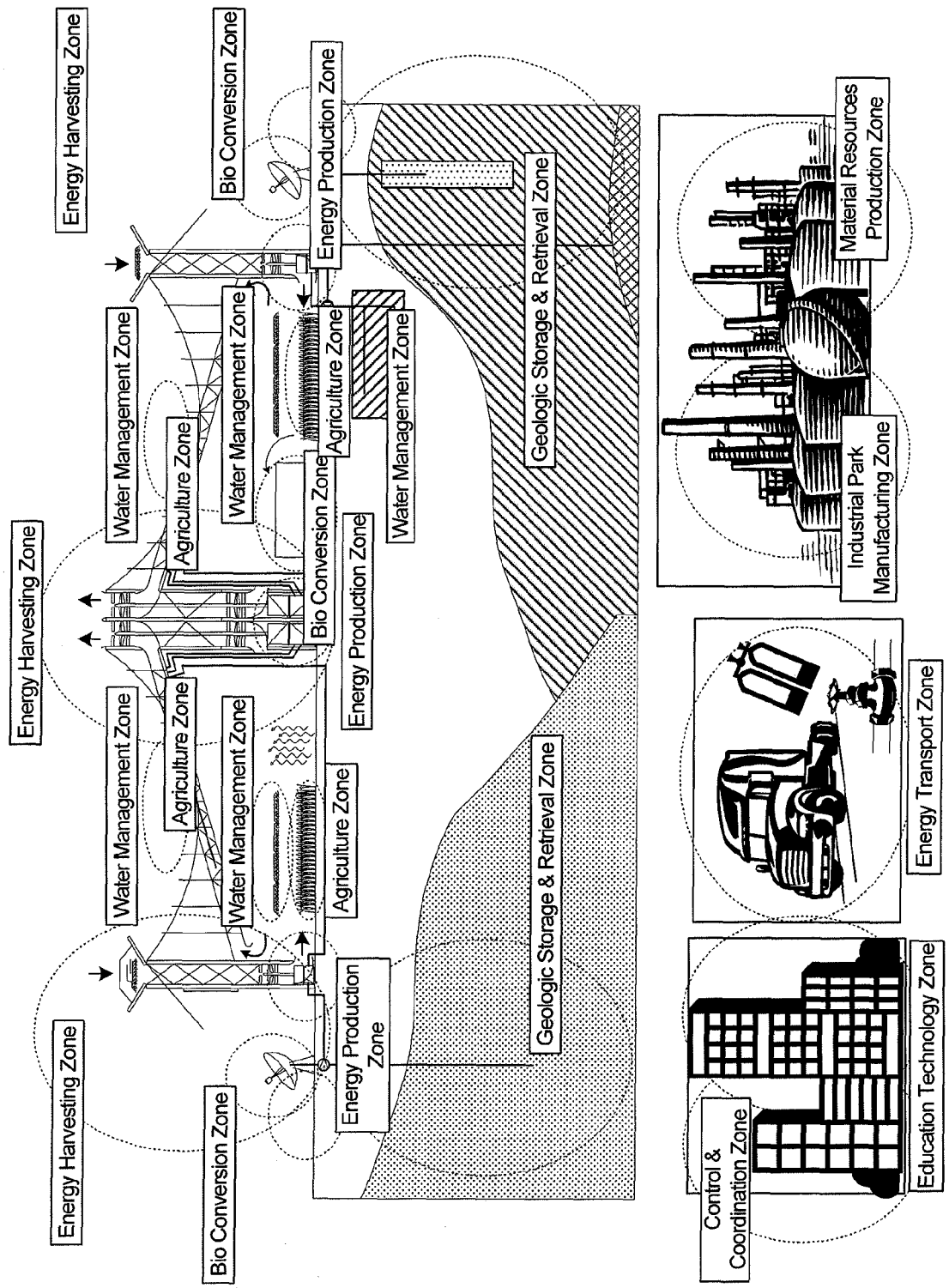
FIG. 1C is a schematic illustrating a land-based system of integrated production of sustainable economic development in accordance with aspects of the disclosure.
Figure 1D:
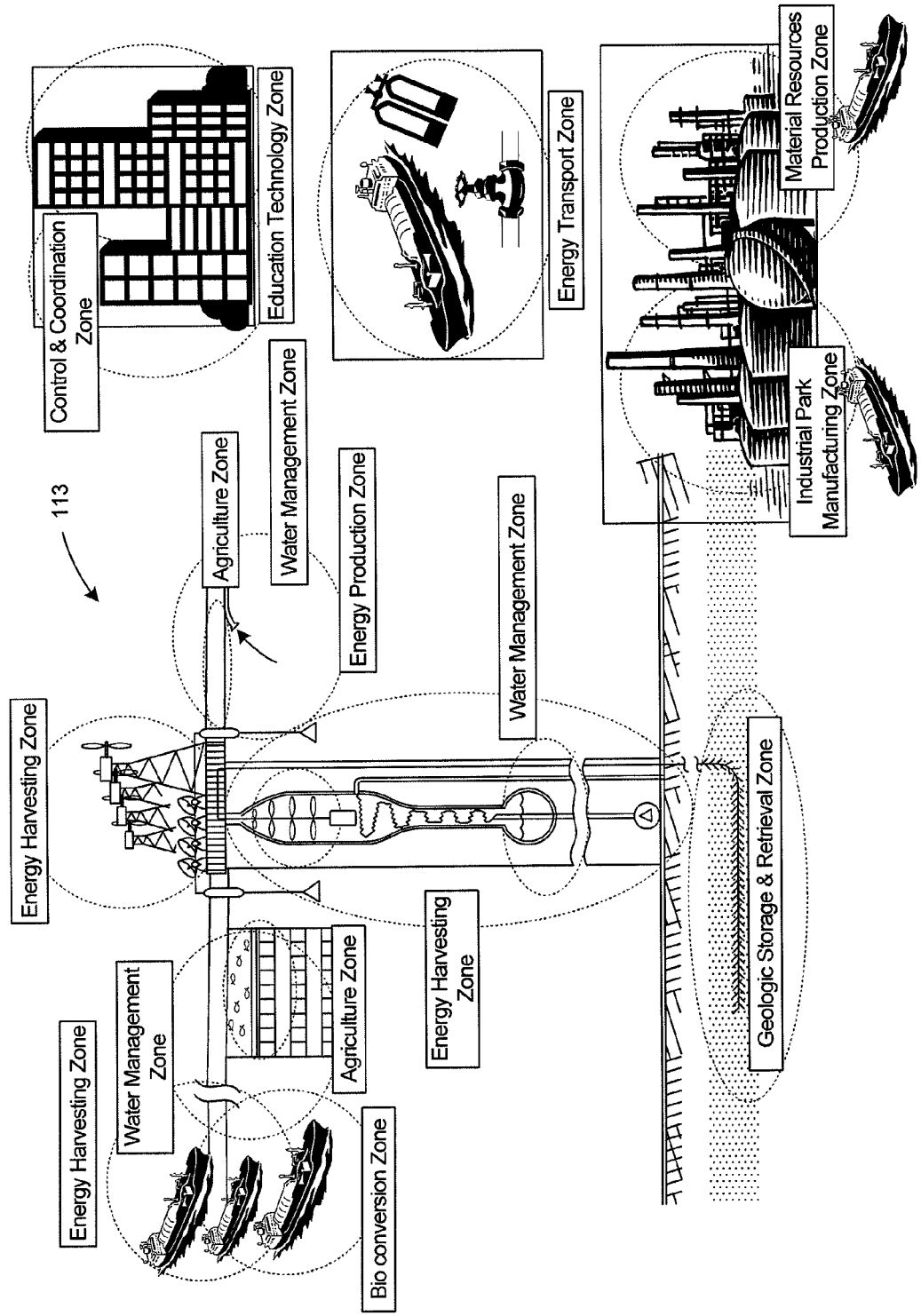
FIG. 1D is a schematic diagram illustrating an ocean-based system of integrated production of sustainable economic development in accordance with aspects of the disclosure.

FIG. 1C is a schematic illustration of a Full Spectrum Integrated Production System 100 showing various exemplary functional zones for a land-based system; FIG. 1D is a schematic illustration of a Full Spectrum Integrated Production System 100 showing various exemplary functional zones for an ocean-based system. The systems shown include an integrated production system on land or ocean with adaptive control of cascading energy conversions and autogenous regeneration of materials resources and production of nutrient regimes. The system includes functional zones for purposes of harvesting and/or generating energy from renewable sources and harvesting material resources from renewable feedstocks that store, retrieve, transport, monitor and control the energy and material resources to achieve improved efficiencies in the production of energy, material resources, and nutrient regimes. Table 1 below expands on exemplary outputs, systems and means associated with the illustrative functional zones.

TABLE 1

Full Spectrum Integrated Production System Functional Zones

| | |
|---|---|
| Full Spectrum Integrated Production System Functional Zones | An integrated production system on land or ocean with adaptive control of cascading energy conversions and autogenous regeneration of materials resources and production of nutrient regimes. The system includes functional zones for purposes of: harvesting and/or generating energy from renewable sources harvesting material resources from renewable feedstocks that stores, retrieves, transports, monitors, and controls said energy and material resources to achieve improved efficiencies in the production of energy, material resources, and nutrient regimes. |

| Zone | Outputs | Systems and Means |
|---|---|---|
| Energy Harvesting Zone | Harvested renewable energy from sources such as: solar wind, geothermal moving water biomass & biowaste engine thermal rejected heat | solar thermal devices wind turbines moving water turbines heat conversion devices electrolyzers adaptive control of autogenous cascading energy conversions |
| Energy Production Zone | Renewable: electricity gaseous fuels (e.g., hydrogen, methane, CNG) liquid fuels (e.g., methane, biodiesel, HyBoost) energy carrier feedstock | hydrogen-fueled internal combustion engines generators biomass/biowaste conversion systems electrolyzers |
| Geologic Storage and Retrieval Zone | amplification of heat energy in stored gases reclamation of existing chemical and trace mineral resources mitigation of the variability of renewable energy sources (e.g., solar, wind) | geothermal reservoirs wind turbines gas pressurization systems heat conversion devices |
| Energy Transport Zone | Delivery of: scalable on-demand electricity gaseous fuels (e.g., hydrogen, methane, CNG) liquid fuels (e.g., methane, biodiesel, hydrogen-enriched fuel) energy carrier feedstock materials resources feedstock | energy storage and filtration system pressurized hydrogen and other gases hydrogen-fueled trucks, barges, ships, and trains gas pipeline grid electricity grid |
| Biowaste/Biomass Conversion Zone | energy fuels energy carrier feedstock materials resources feedstock | biodigesters electrolyzers |
| Agricultural Zone | human, animal, and plan nutrition plant crops animal crops biofuel biomass biowaste | Farms and fisheries with: controlled micro-climates nutrient regimes such as trace minerals and other materials resources to enrich soil and water water reclamation integrated biomass and biowaste harvesting |
| Material Resources Production Zone | chemical and mineral byproducts (e.g., hydrogen, methane, oxides of carbon, oxides of nitrogen, petrochemicals, ash, nitrogen) additional byproducts (e.g., hydrogen, carbon, designer carbons, oxygen, ammonia, fertilizer, methanol) | autogenous regeneration of materials resources from carrier feedstock |
| Industrial Park Manufacturing Zone | Green machines such as: solar thermal devices wind turbines moving water turbines heat conversion devices electrolyzers polymer thin films | pre-manufacturing preparation of feedstock materials resources production zero-emissions manufacturing using renewable hydrogen-fueled |

TABLE 1-continued

Full Spectrum Integrated Production System Functional Zones

| | | |
|---|---|---|
| | engines and generators<br>Other industrial goods:<br>designer carbon<br>industrial diamonds<br>auto, truck, train, & ship<br>parts<br>semiconductors<br>nanotechnologies<br>farm & fishery equipment<br>Consumer durable goods | internal combustion<br>engines (stationary,<br>vehicle) |
| Water<br>Management<br>Zone | water<br>controlled aquatic micro-<br>climate for system<br>processes | production of new water<br>purification of water<br>reclamation of water<br>conservation of water<br>heat sink using water<br>adaptive control of water<br>within the system |
| Control and<br>Coordination<br>Zone | Macro coordination of<br>information across zones to<br>achieve task of zero emissions<br>production of energy, material<br>resources and nutrient regimes | embedded sensing devices<br>in all zones<br>computer monitoring and<br>control using the embedded<br>sensing devices<br>automation<br>robotics<br>information/data<br>management at<br>microscopic levels |
| Education<br>Technology<br>Zone | specialized cross-<br>disciplinary skill<br>development of workforce<br>job creation at each<br>installation site<br>new kinds of energy sector<br>jobs appropriate to<br>integrated renewable<br>energy production,<br>renewable material<br>resource production, and<br>renewable nutrient regime<br>production | integrated training in cross-<br>disciplinary fields<br>application, monitoring, and<br>performance support in the<br>Full Spectrum Integrated<br>Production System<br>environment |

Figure 1E:
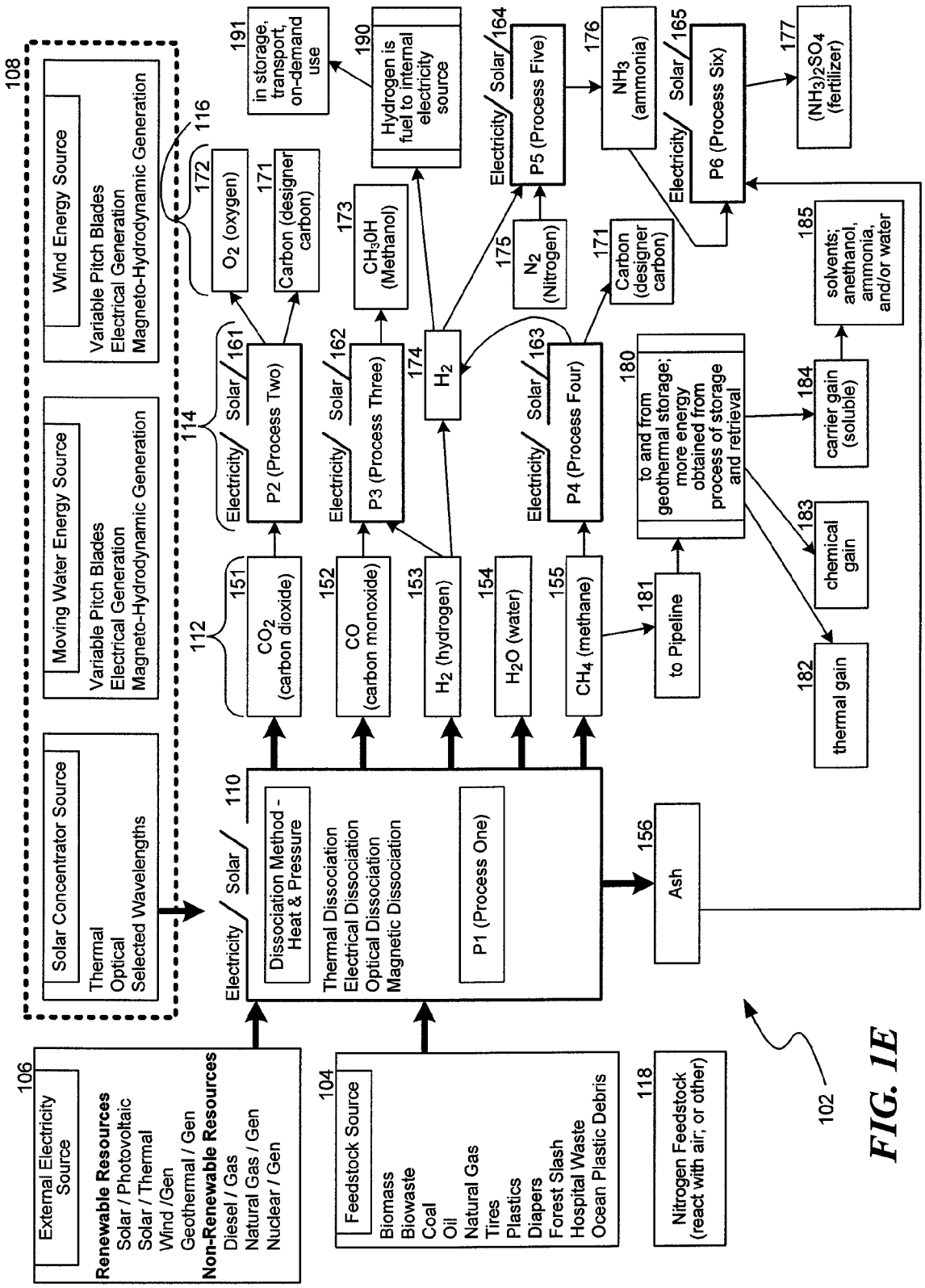
FIG. 1E is a block diagram illustrating a system of sustainable economic development in accordance with aspects of the disclosure.

FIG. 1E is a block diagram illustrating another system 102 of sustainable economic development, such as the production of a resource (e.g., hydrogen and carbon) in accordance with aspects of the disclosure. The system 102 captures and reinvests some or all of the substances and/or byproducts during extraction of the resource using renewable energy sources. Thus, the system facilitates sustainable economic development, such as the harnessing of renewable energy, which is greater than the harnessing of the renewable energy using conventional techniques, among other benefits.

A feedstock source 104 supplies feedstock to the system 102. The feedstock may be any matter or substances that include hydrogen or carbon. Suitable carbon-containing or hydrogen-containing feedstock includes biomass, biowaste, coal, oil, natural gas, tires, plastics, diapers, forest slash, hospital waste, ocean debris, sea water, industrial waste water, agricultural waste water, sewage, landfill waster water, and so on. In some cases, the system may receive a nitrogen-containing feedstock 118, such as air.

An extraction component 110 receives the feedstock 118 from the feedstock source 104. The extraction component is configured to extract resources or other substances from the feedstock, or to otherwise separate the feedstock into different substances. In some cases, the extraction component 110 dissociates supplied feedstock into carbon-containing substances, hydrogen-containing substances, various nutrients and/or ash. The extraction component 110 may extract resources from supplied feedstock using various dissociation, extraction, or separation techniques, including:

Thermal dissociation, which may include adding heat to a substance or substances to produce a reaction;

Electrical dissociation, which may include electrolysis with or without separation of substances, electrodialysis, electroseparation, and so on;

Optical dissociation, which may include using selected wavelengths to dissociate a compound or depolymerize a polymer; and Magnetic dissociation or separation, which may include ferromagnetic dissociation, paramagnetic dissociation, magnetohydrodynamic acceleration, magnetic field deflection of substances, and so on.

Further details regarding suitable extraction, dissociation, and/or separation processes and techniques may be found in priority documents U.S. patent application Ser. No. 12/707,651, filed Feb. 17, 2010 and titled ELECTROLYTIC CELL AND METHOD OF USE THEREOF; U.S. patent application Ser. No. 12/707,653, filed Feb. 17, 2010 and titled APPARATUS AND METHOD FOR CONTROLLING NUCLEATION DURING ELECTROLYSIS; U.S. patent application Ser. No. 12/707,656, filed Feb. 17, 2010 and titled APPARATUS AND METHOD FOR GAS CAPTURE DURING ELECTROLYSIS; which are incorporated by reference in its entirety.

In some cases, the extraction component 110 dissociates the feedstock into various substances using electricity received from an external or internal electricity source 106. Examples of suitable external electricity sources include renewable resources (solar/photovoltaic sources, solar/thermal sources, wind sources, geothermal sources, and so on) or non-renewable sources (diesel generators, natural gas generators, coal or nuclear generators). Examples of suitable internal electricity sources include internal combustion engines, fuel cells, thermoelectric devices, piezoelectric devices, and so on. Some or all of the electricity sources may be configured to receive byproducts or other substances from various components of the system in order fuel or assist in the generation of electricity provided to the extraction component 110.

In some cases, the extraction component 110 dissociates the feedstock into various substances using energy received from a renewable energy source 108. Examples of suitable renewable energy sources include solar concentrators (such as those described herein) and other solar energy sources, moving water energy sources, and/or wind energy sources.

In some cases, the extraction component 110 utilizes energy received from both the electricity source 106 and the renewable energy source 108 to assist in the dissociation of a feedstock into various desired substances. The extraction component may also vary the heat and/or pressure applied to the feedstock during a dissociation process.

The extraction component 110 dissociates a supplied feedstock into various products or byproducts 112, including carbon dioxide ($CO_2$) 151, carbon monoxide (CO) 152, Hydrogen ($H_2$) 153, Water ($H_2O$) 154, Methane ($CH_4$) 155, Ash 156, and/or other substances (not shown). Using the various products 112, the system generates desired resources 116, such as Carbon 171, Ammonia 176, Fertilizer 177, Hydrogen 174, Methanol 173, Oxygen 172, and so on.

The system 102 supplies the various products or byproduct 112 to various resource generation components 160 to generate the desired resources 116. These include:

a resource generation component 161 configured to generate Oxygen 172 and Carbon 171 (e.g., designer Carbon) from Carbon dioxide 151;

a resource generation component 162 configured to generate Methanol 173 from Carbon dioxide 151 or Carbon monoxide 152 and Hydrogen 153;

a resource generation component 163 configured to generate Hydrogen 174 and Carbon 171 from Methane 155;

a resource generation component 164 configured to generate Ammonia 176 from Hydrogen 153 and Nitrogen 175;

a resource generation component 165 configured to generate a suitable Fertilizer 177 from Ammonia 176 and Ash 156; and/or other resource generation components (not shown).

Further details regarding operation of the resource generation components will be discussed with respect to FIGS. 3A-3E.

In addition to generating resources using products or byproducts 112, the system 102 may store or otherwise utilize products 112 or generated or desired resources 116. In some cases, the system transfers the Methane 155 to a geothermal storage source 180 via a pipeline 181. The storing, and subsequent retrieval, of the methane may enable the system to obtain energy, such as by thermal gain 182, chemical gain 183, and/or a carrier gain 184 to produce certain solvents 185, such as methanol, ammonia, and/or water.

Illustratively, sustainable economic development is provided by conversion of substances 110 containing carbon into carbon-reinforced materials and components for various applications including equipment that harnesses renewable solar, wind, moving water, and/or geothermal resources. Such applications of carbon as an equipment component provides many times greater production of energy in comparison with the one-time combustion of such carbon. In other instances such carbon is converted into transportation equipment components that are lighter than aluminum and stronger than steel to reduce the curb weight and to improve fuel economy and reduce adverse emissions. In other applications carbon can be specialized into heat sinks and heat transfer components that conduct more heat than copper in equivalent cross-sectional area to reduce the weight and increase the range of suitable operating temperatures. Among the multitude of additional applications, specialized carbon deposits and/or coatings provide benefits ranging from diamond-like hardness and corrosion resistance to optically black or selective surfaces.

Hydrogen is co-produced in virtually all instances that carbon is extracted for purposes of being incorporated in durable goods. Production of hydrogen by dissociation of a source compound such as methane is potentially very inexpensive. This is because the energy required for extracting hydrogen from most hydrocarbons is much less than the energy required to produce hydrogen by dissociation of water by thermal, electrical, radiation, or magnetic separation technologies.

The potential for sustainable economic development is bolstered by the use of hydrogen in the world's existing population of about one billion engines because appropriate technologies for such conversion from gasoline or diesel fuel to operation on hydrogen provides a much greater return on investments previously made to purchase such engines. Engines converted to operation on hydrogen by the technologies disclosed in U.S. patent application Ser. No. 12/653,085; U.S. patent application Ser. No. 12/841,170; U.S. patent application Ser. No. 12/804,510; U.S. patent application Ser. No. 12/841,146; U.S. patent application Ser. No. 12/841,149; U.S. patent application Ser. No. 12/841,135; U.S. patent application Ser. No. 12/841,509; and U.S. patent application Ser. No. 12/804,508 can produce more power when needed, last longer with less maintenance, and actually clean the air that enters their combustion chambers.

Thus increasing the returns on existing engine investments by reducing the cost of fuel per horsepower-hour, increasing the power-production capacity, reducing the cost of maintenance, and actually cleaning the air makes capital available for acquisition of carbon-reinforced equipment to harness renewable resources. This provides anti-inflationary economic development a ever-increasing capacity for production of goods and services as renewable solar, wind, moving water, and geothermal resources are harnessed. Similarly renewable nutrients for biomass and food production are provided as a result of this shift from dependence upon fossil fuels and waste disposal practices such as landfills that intentionally provide many decades of confinement of essential trace minerals, sulfur donors and fixed nitrogen.

In some cases, the system transfers the hydrogen 174 to storage 191 or to one or more energy sources 190. For example, the hydrogen 174 may fuel an internal electricity source 106, such as an engine or fuel cell used to assist in dissociation of feedstock.

Thus, the system 102 uses renewable resources and renewable energy to create refined renewable resources and energy having a greater economic value than what would be created using conventional processes, among other benefits. The system uses the refined renewable resources and energy to harvest new renewable resources and energy in a sustainable, non-polluting, and non-depleting manner. That is, the system achieves an economic multiplier effect for resources supplied to the system by constantly reinvesting the resources into the system, such as into the renewable energy sources and the various processes within the system.

For example, the system 102 dissociates methane and hydrogen from a supplied biomass, harvests renewable energy and resources, such as carbon, from the methane and hydrogen, and uses the carbon to harvest more biomass and methane to harvest more carbon and hydrogen, and so on. Thus, the system takes a small amount of a resource, such as hydrogen, from a supplied energy source, and constantly reinvests the resource, other resources, and other byproducts into different energy sources and processes to capture larger amounts of the supplied resource from various resources within the system. This leads to a multiplying effect on the amounts of various resources and energy harvested from renewable energy sources within the system, leading to the sustainable economic development of resources and energy from renewable energy sources, among other benefits.

Illustratively hydrogen can be reacted with carbon dioxide that is discarded from sources such as bakeries, breweries, cement plants, or fossil fired power plants to produce various substances including solvents such as methanol, ethanol, butanol or tetrahydrofuran. Such substances can be utilized to provide compact storage and transport of hydrogen including the multifunctional purpose of serving as a solvent for dissolving a wide range of polar and nonpolar materials. Retrieval from storage of such solvents in depleted oil and natural gas wells enables extraction of renewable thermal energy along with hydrocarbons that otherwise would have remained un-produced from such wells. Thus vast storage capabilities are provided for renewable hydrogen through the utilization of existing pipelines and substantially depleted hydrocarbon formations.

In operation, an energy-conversion cycle can be combined with a mineral extraction benefit. Liquid hydrogen-storage solvent is delivered to a geothermally warm formation. In one embodiment the liquid is returned to the surface for extraction of dissolved values and conversion of energy delivered by geothermally heated vapor expansion. In some instances it is desired to operate a portion of the resulting circuit near or above the critical temperature and pressure of the solvent. In another embodiment the pressure provided by the column height and/or the pressure produced by vaporization of the liquid as a result of heat gain may be harnessed at or near the storage depth. After extraction of desired mineral values and energy the vapors are cooled to provide liquid by heat rejection to the air or water or other substances within the system. The fluid such as liquid condensate thus produced is utilized to continue the selected process of energy and mineral value extraction from the geothermal formation. Thus the process provides a multiplying effect for renewable energy production along with supplies of additional hydrogen, materials and feedstocks that can serve as carbon donors for purposes of manufacturing equipment to harness renewable energy resources.

Using Renewable Energy to Produce Resources

Figure 2A:
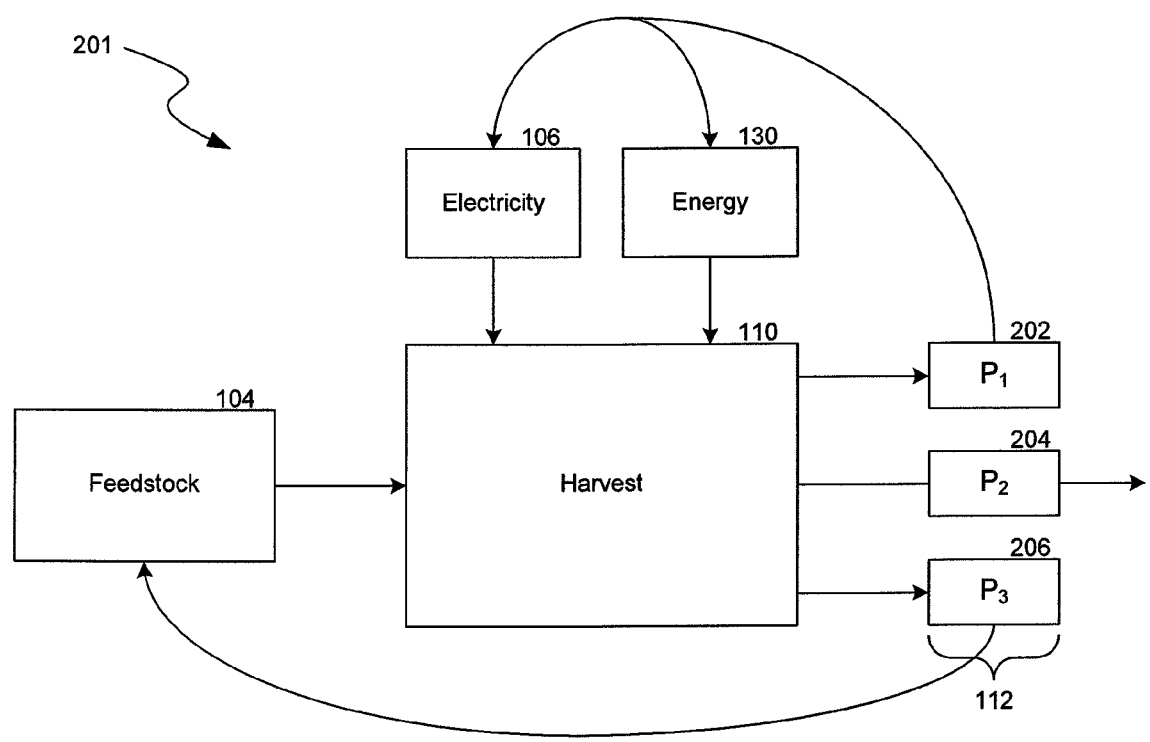
FIG. 2A is a block diagram illustrating some components of the system used to harvest resources from feedstock in accordance with aspects of the disclosure.

The inventor has realized that utilizing renewable energy sources during extraction of resources enables a system to economically sustain and generate resources, feedstock, and other substances that enter or exit from the system. FIG. 2A is a block diagram illustrating some components 201 of system 102 used to harvest resources from feedstock. The system 102 utilizes energy sources 108, such as renewable energy sources, and electricity sources 106 to assist in harvesting desired resources from feedstock supplied by a feedstock source 110. A harvest component, such as the extraction component 110 of FIG. 1, harvests various substances or products 112 from feedstock supplied by the feedstock source 110.

Using the various components and processes described herein, the system 102 may harvest substances for a number of different purposes, including substances 202 harvested to supply fuel to the electricity source 106 or the renewable energy source 108 (e.g., to provide fuel for a fuel cell or a solar concentrator), substances 204 harvested to be transferred out the system (e.g., for use externally, to be stored, and so on), and/or substances 206 harvested to supply more feedstock to the feedstock source 110.

Figure 2B:
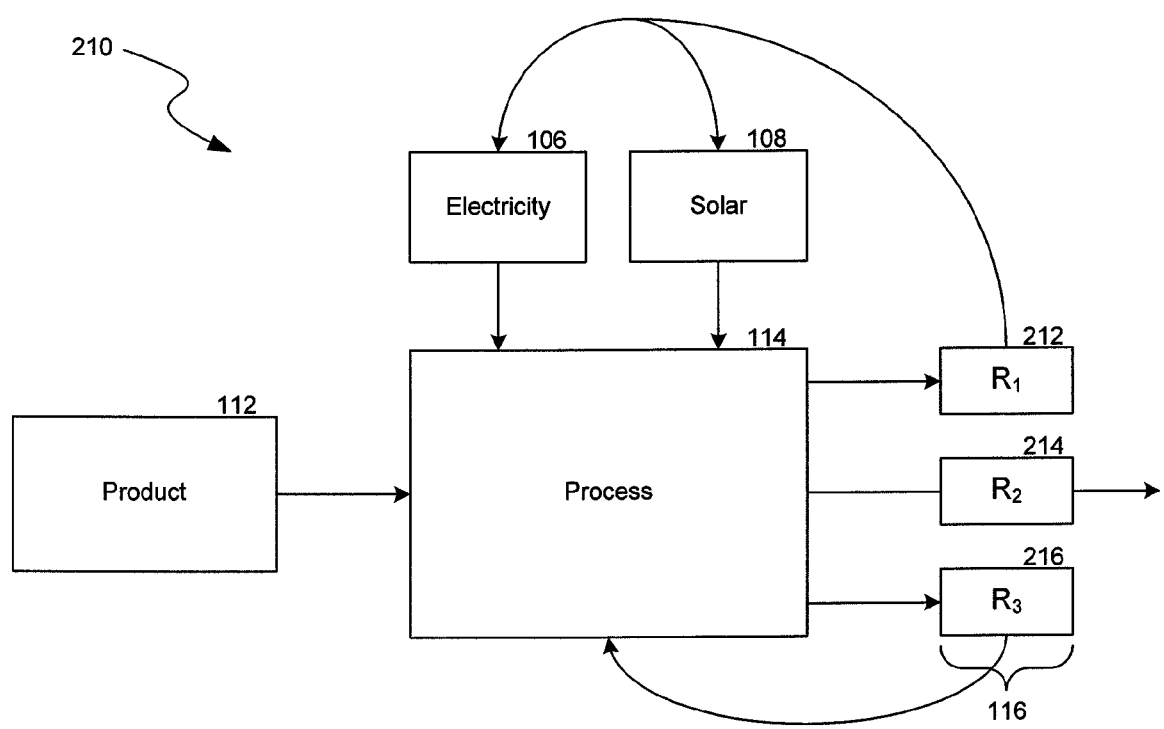
FIG. 2B is a block diagram illustrating some components of the system used to generate resources from products or byproducts during the harvesting of resources from supplied feedstock in accordance with aspects of the disclosure.

FIG. 2B is a block diagram illustrating some components 210 of system 102 used to generate resources from products or byproducts during the harvesting of resources from supplied feedstock. A product 112 is supplied to a resource generation component 114, which utilizes energy received from an electricity source 106 or a renewable energy source 108 to generate one or more resources 116.

Using the various components and processes described herein, the system 102 may generate resources for a number of different purposes, including resources 212 harvested to supply fuel to the electricity source 106 or the renewable energy source 108 (e.g., to provide fuel for a fuel cell or working fluid or fuel during night-time operation of a solar concentrator system), resources 214 harvested to be transferred out of the system (e.g., for use externally, to be stored, and so on), and/or substances 216 harvested to supply substances to a resource generation component 160 for resource generation.

As discussed above, the system utilizes a variety of resource generation components 160 in order to provide for the sustainable production of desired resources. FIGS. 3A-3E are block diagrams illustrating the operation of resource generation components 160 within the system 110.

Figure 3A:
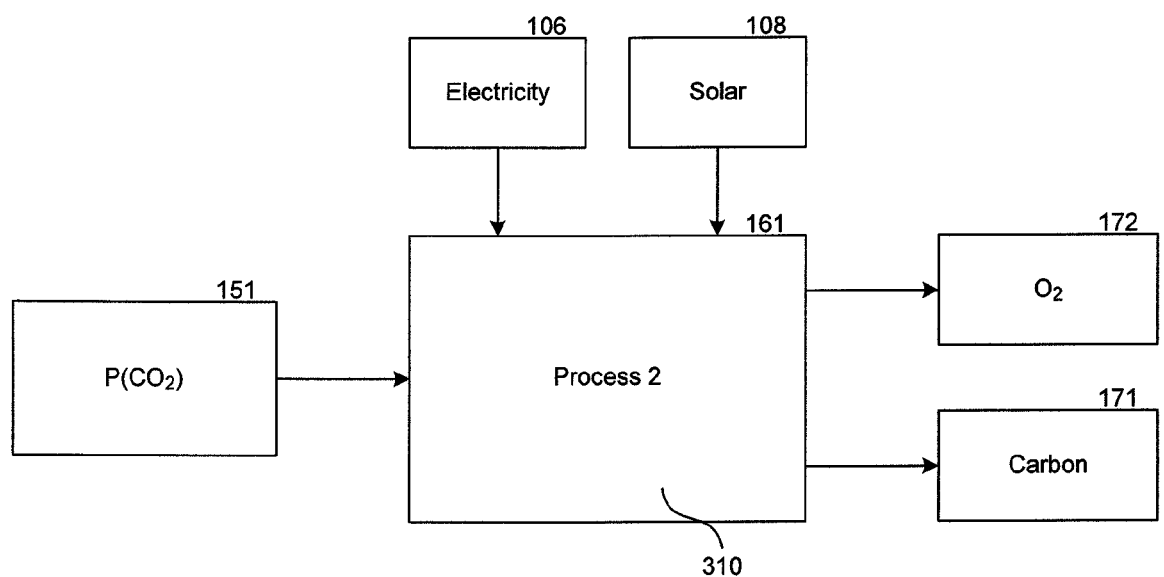
FIGS. 3A-3E are block diagrams illustrating the operation of resource generation components within the system in accordance with aspects of the disclosure.

FIG. 3A shows a resource generation component 161 configured to generate Oxygen 172 and Carbon 171 (e.g., designer carbon) from carbon dioxide 151. The resource component 161, utilizing energy from an electricity source 106 and/or a renewable energy source 108, performs various processes 310, such as the dissociation of a carbon donor such as carbon dioxide or carbon monoxide to provide carbon and oxygen as shown. In operation such carbon donors are supplied as fluids such as gas or liquid to a heat input zone such as shown in a helical conveyer having a counter-current exchange to energy addition zone of a concentrated solar radiation to provide endothermic heat and/or radiation induced dissociation as generally summarized in Equation 310 or 310':

$$CO_2 + ENERGY \rightarrow C + 0.5 O_2 \qquad \text{Equation 310}$$

$$CO + ENERGY \rightarrow C + 0.5 O_2 \qquad \text{Equation 310'}$$

Figure 3B:
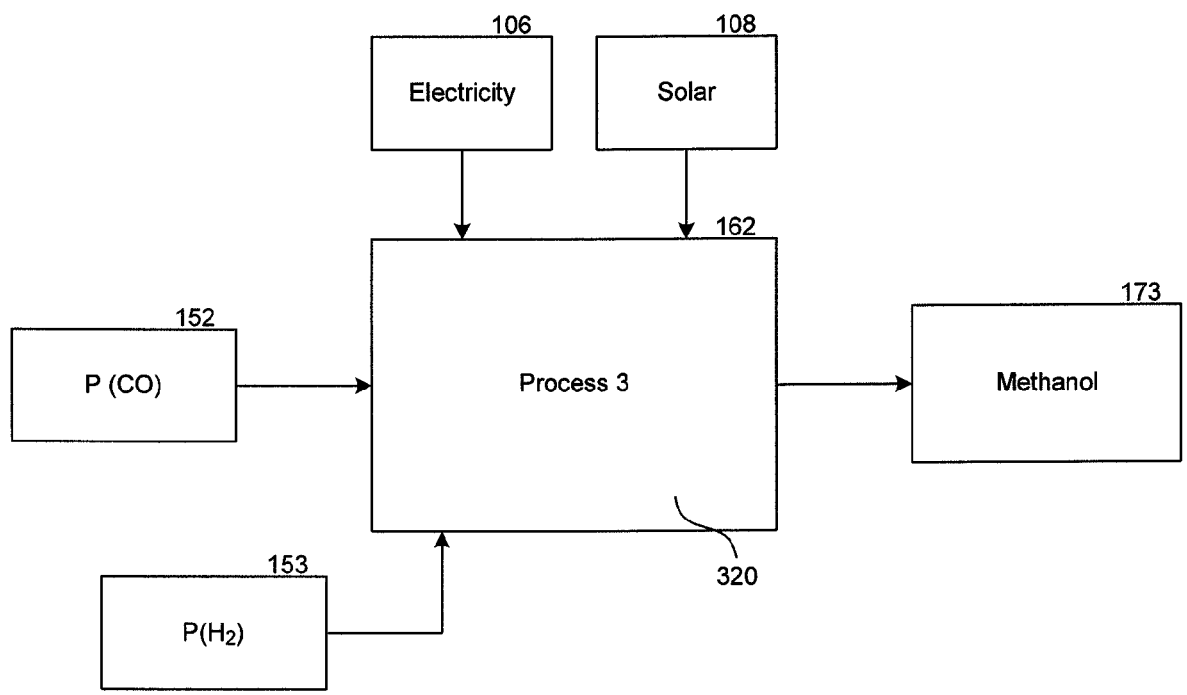

FIG. 3B shows a resource generation component 162 configured to generate Methanol 173 from carbon dioxide and/or carbon monoxide 152 and hydrogen 153. The resource component 162, utilizing energy from an electricity source 106 and/or a renewable energy source 108, performs various processes 320, such as the pressurization of the reactants for illustrative processes such as those summarized in Equations 320 and 320':

$$CO + 2H_2 \rightarrow CH_3OH \qquad \text{Equation 320}$$

$$CO_2 + 3H_2 \rightarrow CH_3OH + H_2O \qquad \text{Equation 320'}$$

In operation such pressurization may be provided by dissociation of various hydrogen donors such as water or a hydrocarbon or another selected compound in which the volume of hydrogen produced is prevented from expansion for the purpose of producing the desired pressure to facilitate reactions such as shown in Equations 320 and 320'.

Figure 3C:
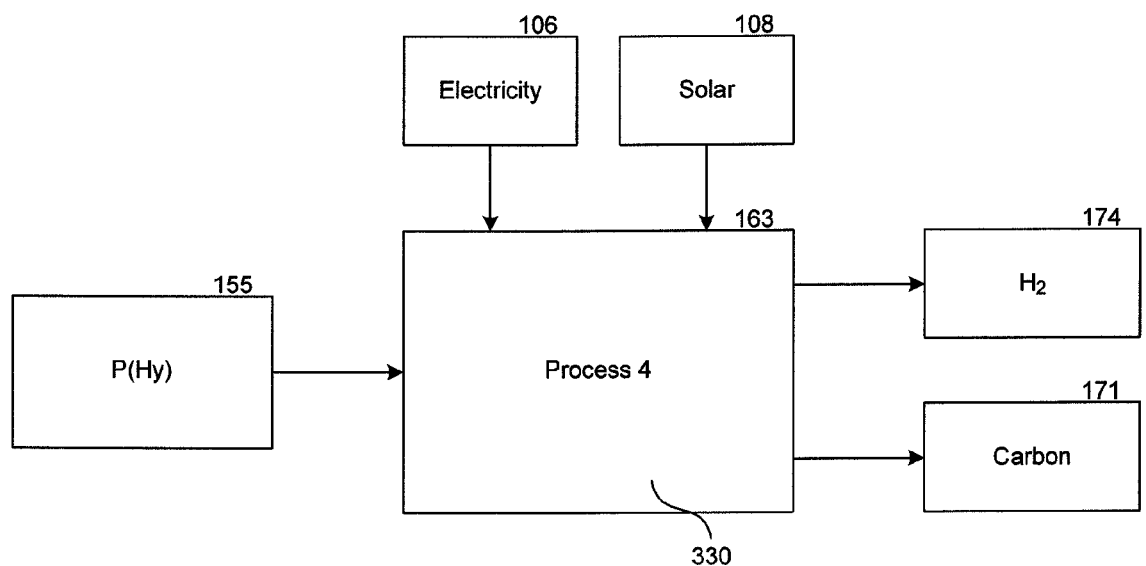

FIG. 3C shows a resource generation component 163 configured to generate hydrogen 174 and Carbon 171 from Methane 155. The resource component 163, utilizing energy from an electricity source 106 and/or a renewable energy source 108, performs various processes 330, such as the thermal, electrical, and/or magnetic energy conversion process of inducing dissociation such as summarized in Equations 330 and 330':

$$CH_4 + ENERGY \rightarrow C + 2H_2 \quad \text{Equation 330}$$

$$CxHy + ENERGY \rightarrow xC + 0.5yH_2 \quad \text{Equation 330'}$$

Figure 3D:
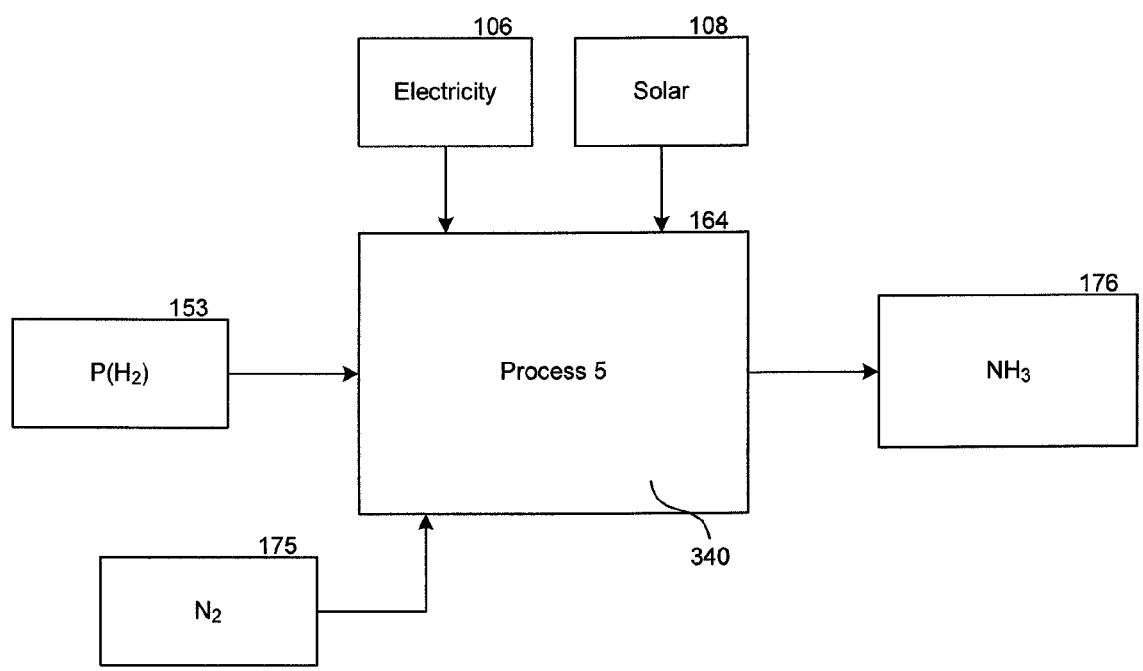

FIG. 3D shows a resource generation component 164 configured to generate ammonia 176 from hydrogen 153 and nitrogen 175. The resource component 164, utilizing energy from an electricity source 106 and/or a renewable energy source 108, performs various processes 340, such as the Haber-Bosch process. One embodiment provides for selectively admitting and transporting hydrogen from a mixture of substances for the purpose of reacting such hydrogen at or near the delivery interface with nitrogen as disclosed in co-filed applications incorporated above by reference, which provides for nitrogen to be sequestered from a source such as ambient air by combustion of surplus hydrogen in an engine. Equation 340 summarizes the process for combining atmospheric oxygen with surplus hydrogen to produce separable streams of water and nitrogen.

$$Air + H_2 \rightarrow H_2O + N_2 + H_2 + Argon \quad \text{Equation 340}$$

$$H_2 + N_2 + Argon \rightarrow NH_3 + Argon \text{ Equation} \quad 340'$$

In operation air enters the combustion chamber of an engine that may drive a load such as a pump or electricity generator. Surplus hydrogen is utilized to deplete the oxygen in the combustion chamber by forming water vapor which is subsequently condensed or removed by pressure swing or temperature swing media from the exhaust stream. The remaining exhaust stream of nitrogen with much lower concentrations of other components such as argon is pressurized and presented for reaction with hydrogen to produce ammonia as summarized by equation 340'. Ammonia is separated by condensation or collection by media in temperature swing or pressure swing systems along with collection of values such as argon.

Figure 3E:
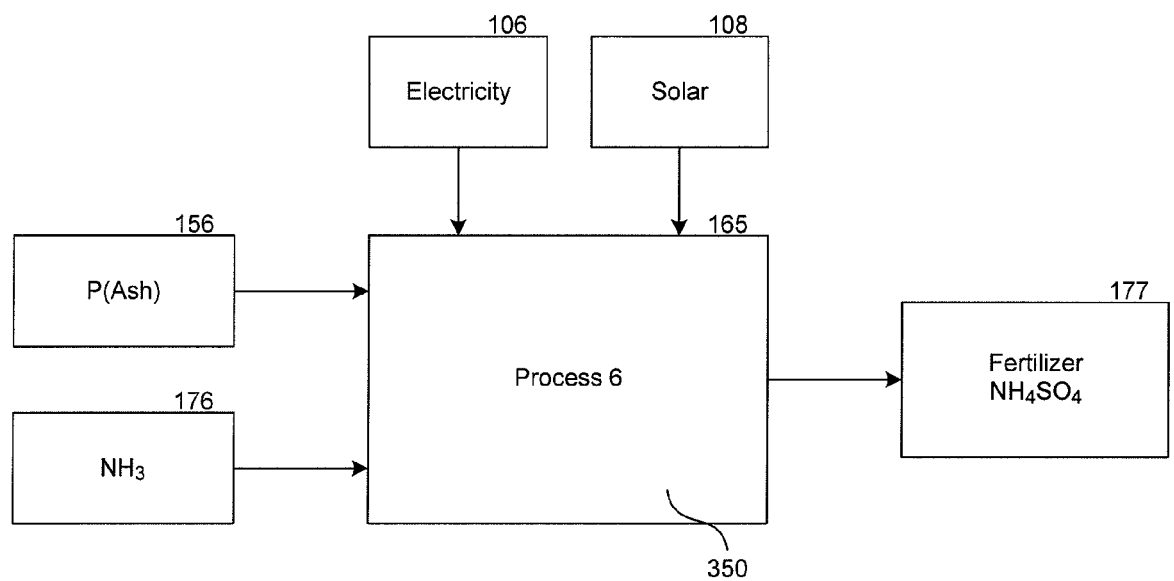

FIG. 3E shows a resource generation component 165 configured to generate fertilizer 177 from ammonia 176 and ash 156. The resource component 165, utilizing energy from an electricity source 106 and/or a renewable energy source 108, performs various processes 350 such as in an illustrative embodiment, ammonia is reacted with sulfur dioxide and water to produce ammonium sulfate as generally summarized in Equation 350, which is not balanced:

$$NH_3 + SO_2 + H_2O \rightarrow NH_4SO_4 \quad \text{Equation 350}$$

In operation a suitable reactor provides for a sulfur source such as a suitable oxide of sulfur including sulfur dioxide to react in the presence of water and oxygen. By utilization of surplus ammonia attractive conversion rates are achieved. Soil or hydroponic fluid tests are made to determine the need for additions of minerals such as phosphorus, potassium, iron, manganese, magnesium, calcium, boron, selenium, molybdenum and so forth and a suitable formulation with such additions is provided.

Of course, the system may utilize other resource generation components or other processes to produce the resources used by the system.

Harnessing Energy from Renewable Energy Sources Using Extracted Resources

Figure 4:
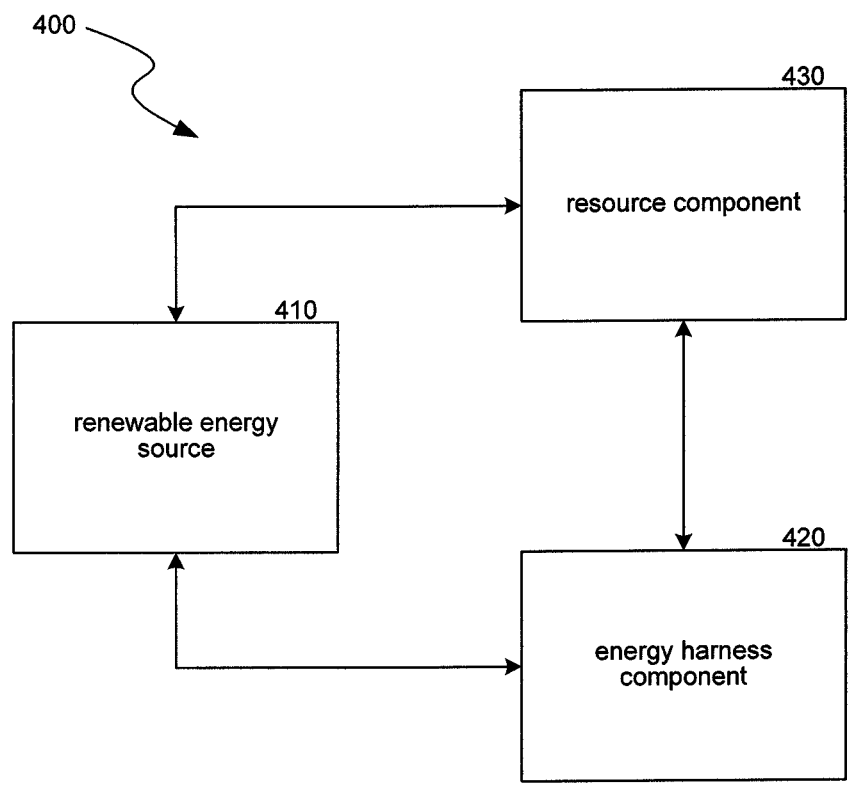
FIG. 4 is a block diagram illustrating an energy harnessing system or harnessing energy from renewable resources in accordance with aspects of the disclosure.

As discussed herein, the system 102 utilizes some or all of the components described herein in order to generate desired resources, such as hydrogen or carbon. The system uses these resources for variety of purposes, including using the generated resources to harness energy from renewable energy sources. FIG. 4 is a block diagram illustrating an energy harnessing system 400 for harnessing energy from renewable resources.

The energy harnessing system 400 includes a renewable energy source 410, such as a solar energy source, a wind energy source, a geothermal energy source, a moving water energy source, and so on. The renewable energy source 410 provides energy to an energy component 420, which facilitates the harnessing of energy from the renewable energy source 410. The energy component 420 receives one or more resources from a resource component 430. The resource component 430 may be various components of the system 102, including the extraction component 110, one or more resource generation components 114, the pipeline 180, the storage/transport component 191, and/or other components.

Figure 5:
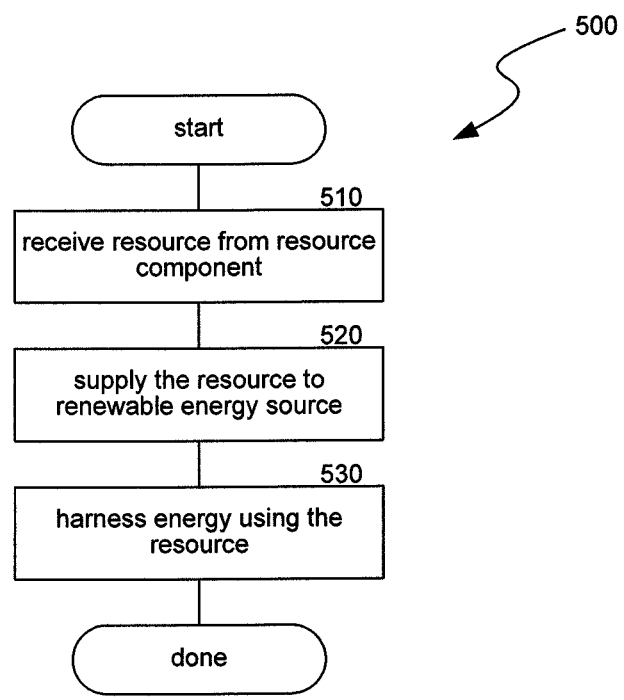
FIG. 5 is a flow diagram illustrating a routine for harnessing energy using a generated resource in accordance with aspects of the disclosure.

In some cases, the energy component 420 provides a resource supplied by the resource component 430 to the renewable energy component 410, enabling the renewable energy component to harness a greater amount of energy than would be harnessed without the supplied resource. FIG. 5 is a flow diagram illustrating a routine 500 for harnessing energy using a generated resource.

In step 510, the energy harnessing system 400 receives a resource into the resource component 430. For example, the energy harnessing system 400 may be part of the system 102, and receive a resource from the extraction component 110 (i.e., after dissociation of a feedstock) or from one or more resource generation components 114.

In step 520, the energy harnessing system 400, possibly via the energy component 420, supplies the received resource to the renewable energy source 410. For example, the system 400 supplies the renewable energy source with one or more resources that may be used as fuel or otherwise enhance a reaction that occurs at the renewable energy source 410.

In step 530, the renewable energy source 410 harnesses energy using the supplied resource. The renewable energy source may implement or otherwise utilize the resource during the capture of energy in order to harness a greater amount of energy than would otherwise be captured without the supplied resource.

For example, the energy harnessing system 400 may facilitate the harnessing of solar energy at a solar collector by supplying oxygen to the solar collector, combusting the oxygen to raise the temperature of a heat zone in which the solar collector focuses received solar energy, and capturing energy from the heat zone. Further details regarding the harnessing of energy by supplying renewable resources to renewable energy sources may be found in copending applications referenced and incorporated above.

Figure 6:
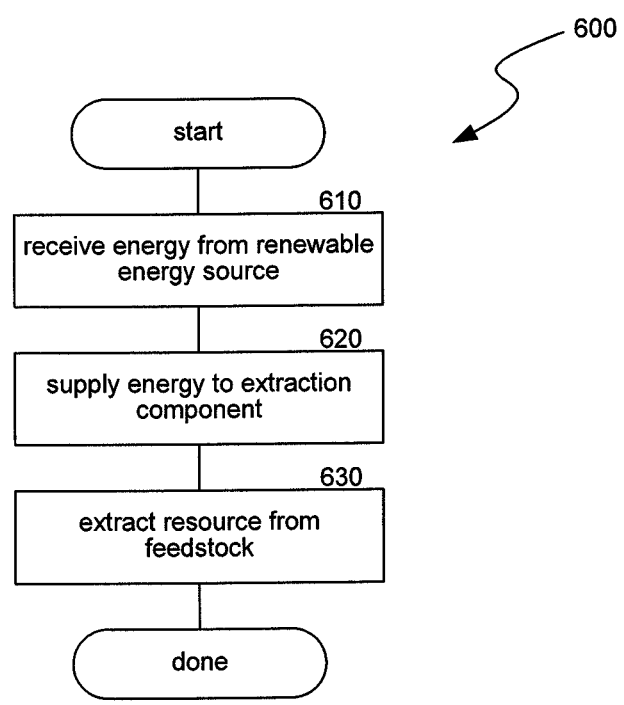
FIG. 6 is a flow diagram illustrating a routine for extracting or generating a resource using energy from a renewable energy source in accordance with aspects of the disclosure.

In some cases, the renewable energy component 410 provides energy to the resource component 430 to facilitate the extraction or generation of a resource. FIG. 6 is a flow diagram illustrating a routine 600 for extracting or generating a resource using energy from a renewable energy source.

In step 610, the energy harnessing system 400 receives energy from the renewable energy source. For example, the system may receive energy from a solar energy source, a wind energy source, a moving water energy source, and so on. The received energy may be energy collected from the source, or may be energy collected from other resources that received the energy from the renewable energy source.

In step 620, the energy harnessing system 400 supplies the energy to an extraction component or a resource generation component. For example, the system 400 may supply the energy to the extraction component, such as an extraction or dissociation component 140 that performs electrolysis to separate hydrogen and oxygen from feedstock.

In step 630, the energy harnessing system 400 extracts or generates a resource using the supplied energy. The extraction component 110 or resource generation component 114 may implement or otherwise utilize the supplied energy to control or otherwise affect an extraction or generation process, such as an electrolysis or combustion of substances.

For example, the energy harnessing system 400 may facilitate the production of hydrogen and oxygen from water in an electrolytic cell by supplying electricity collected from a solar energy source to electrodes of the electrolytic cell, which applies a voltage across the electrodes and dissociates the water into hydrogen and oxygen. Further details regarding the extraction or generation of resources using renewable energy sources may be found in co-pending applications incorporated by reference above.

As discussed herein, energy and/or resources harnessed within the energy harnessing system 400 may be utilized by the system 102 to perform some or all of the processes of the system 102 in order to produce desired resources. For example, the system 102 may receive hydrogen extracted using the energy harnessing system 400 and combust some of the hydrogen with air to generate water and nitrogen, and react some of the hydrogen with the generated nitrogen to produce ammonia or ammonia derivatives. In another example, the system 102 may receive hydrogen extracted using the energy harnessing system 400 and react the hydrogen with generated carbon to produce methane. In another example, the system 102 may receive hydrogen extracted using the energy harnessing system 400 and react the hydrogen with an oxide of carbon to produce a resource of carbon, hydrogen, and oxygen.

Thus, the system harnesses energy in a sustainable manner by providing energy to resource extraction/generation components, which in turn supply resources to renewable energy sources. Such cyclical behavior enables greater production of resources, greater amounts of harvested energy, and sustainable economic development focused on the renewable production of resources and the renewable harnessing or capturing of energy, among other benefits.

The various methods, components, and systems described herein simultaneously produce the renewables of the system (e.g., energy, material resources, and nutrient regimes) in an interrelated and sustainable fashion. Such interrelated production contributes to greater yields of resources and energy than yields from conventional systems, because the system utilized resources more efficiently. The efficient utilization leads to greater amounts of energy captured from renewable energy sources (e.g, solar, wind, water), and, therefore, greater economic development.

CONCLUSION

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the disclosure can be modified, if necessary, to employ fuel injectors and ignition devices with various configurations, and concepts of the various patents, applications, and publications to provide yet further embodiments of the disclosure.

These and other changes can be made to the disclosure in light of the above-detailed description. In general, in the following claims, the terms used should not be construed to limit the disclosure to the specific embodiments disclosed in the specification and the claims, but should be construed to include all systems and methods that operate in accordance with the claims. Accordingly, the invention is not limited by the disclosure, but instead its scope is to be determined broadly by the following claims.

I claim:

1. A system for sustainable economic development, the system comprising:
    an extraction component, wherein the extraction component is configured to extract elemental carbon from a biomass using dissociation; and
    an energy component, wherein the energy component is configured to harness energy from a renewable energy source; the extraction component configured to receive energy from the energy component;
    the energy component comprising at least a portion of the extracted elemental carbon, forming an autogenous energy cascade within the system.

2. The system of claim 1, wherein the energy component is configured to harness from the renewable energy source an amount of energy greater than an amount of energy harnessed from oxidizing the extracted elemental carbon using a combustion engine, a fuel cell, or a thermoelectric cell.

3. The system of claim 1, further comprising:
    a byproduct component, wherein the byproduct component is configured to:
        generate a byproduct using the renewable energy source and one or more non-carbon based substances extracted from the biomass by the extraction component; and
        provide the generated byproduct to the renewable energy source.

4. The system of claim 1, further comprising:
    a byproduct component, wherein the byproduct component is configured to generate a byproduct using the renewable energy source and one or more non-carbon based substances extracted from the biomass by the extraction component.

5. The system of claim 1, wherein the extraction component includes a dissociation component configured to thermally dehydrogenate the biomass.

6. The system of claim 1, wherein the extraction component includes a dissociation component configured to electrically dehydrogenate the biomass.

7. The system of claim 1, wherein the extraction component includes a dissociation component configured to optically dehydrogenate the biomass.

8. The system of claim 1, wherein the extraction component is configured to receive energy from the energy component during extraction of the elemental carbon from the biomass.

9. The system of claim 1, wherein the renewable energy source is a solar concentrator.

10. The system of claim 1, wherein the renewable energy source is a moving water energy source.

11. The system of claim 1, wherein the renewable energy source is a wind energy source.

12. A system for sustainable economic development, the system comprising:
   a feedstock component, wherein the feedstock component provides a substance containing carbon into the system;
   an extraction component; wherein the extraction component dissociates the feedstock into at least two byproducts; at least one of the byproducts containing carbon;
   a resource extraction sub-system for extracting a desired resource from the feedstock byproducts, wherein the resource extraction sub-system includes:
      a resource generation component; wherein the resource generation component dissociates elemental carbon from the byproduct containing carbon; and
      an energy component, wherein the energy component is configured to provide energy to the resource generation component to assist in separation of the desired resource from the feedstock byproduct;
   an additional resource generation sub-system for generating at least one additional resource from at least one feedstock byproduct or at least one byproduct within the resource generation component after separation of the desired resource from the feedstock, wherein the additional resource generation sub-system includes:
      a byproduct reception component, wherein the byproduct reception component is configured to receive one or more byproducts from the feedstock or the resource generation component; and
      an energy component, wherein the energy component is configured to provide energy to convert the one or more byproducts in the byproduct reception component into additional resources;
   byproducts from the feedstock or the resource generation component being reinvested into at least one of the resource generation component, the extraction component, the resource extraction sub-system energy component, or the additional resource generation sub-system energy component, forming an autogenous energy cascade within the system.

13. The system of claim 12, wherein the resource generation component is a dissociation component that performs thermal dissociation to separate the desired resource from the provided feedstock.

14. The system of claim 12, wherein the resource generation component is a dissociation component that performs electrical dissociation to separate the desired resource from the provided feedstock.

15. The system of claim 12, wherein the resource generation component is a dissociation component that performs optical dissociation to separate the desired resource from the provided feedstock.

16. The system of claim 12, wherein the resource generation component is a dissociation component that performs magnetic dissociation to separate the desired resource from the provided feedstock.

17. The system of claim 12, wherein the energy component of the resource extraction sub-system is a renewable energy component.

18. The system of claim 12, wherein the energy component of the resource extraction sub-system is a solar concentrator.

19. The system of claim 12, wherein the energy component of the resource extraction sub-system is a moving water energy source.

20. The system of claim 12, wherein the energy component of the resource extraction sub-system is a wind energy source.

21. The system of claim 12, wherein the byproducts from the feedstock or the resource generation component include carbon dioxide and resources generated include oxygen and carbon.

22. The system of claim 12, wherein the byproducts from the feedstock or the resource generation component include carbon monoxide and hydrogen and a generated resource includes methanol.

23. The system of claim 12, wherein the byproducts from the feedstock or the resource generation component include methane and resources generated include hydrogen and carbon.

24. The system of claim 12, wherein the byproducts from the feedstock or the resource generation component include hydrogen and resources generated include ammonia.

25. The system of claim 12, wherein the byproducts from the feedstock or the resource generation component include ash and resources generated include fertilizer.

26. A method for sustainable economic development, the method comprising:
   non-catalytically dissociating two or more substances from a feedstock, wherein dissociating the two or more substances from the feedstock includes providing energy from a renewable energy source to assist in performing the dissociation; and
   extracting one or more resources, including elemental carbon, from at least one of the two or more dissociated substances using the renewable energy source;
   forming an autogenous energy cascade by reinvesting at least a portion of the one or more resources into either of the steps of: (a) dissociating the two or more substances; or (b) extracting one or more resources.

27. The method of claim 26, wherein the at least one dissociated substance includes carbon dioxide.

28. The method of claim 26, wherein the at least one dissociated substance includes carbon monoxide.

29. The method of claim 26, wherein the at least one dissociated substance includes methane.

30. The method of claim 26, further comprising:
   providing one of the two or more dissociated substances that does not contain carbon to the renewable energy source.

31. The method of claim 26, further comprising:
   when one of the two or more dissociated substances is hydrogen, providing the hydrogen to the renewable energy source.

32. The method of claim 26, wherein one of the dissociated substances does not include carbon, the method further comprising:
   providing the one dissociated substance that does not include carbon to the renewable energy source to generate methanol.

33. The method of claim 26, wherein one of the dissociated substances does not include carbon, the method further comprising:
   providing the one dissociated substance that does not include carbon to the renewable energy source to generate ammonia.

34. The method of claim 26, wherein one of the dissociated substances does not include carbon, the method further comprising:
   providing the one dissociated substance that does not include carbon to the renewable energy source to generate fertilizer.

* * * * *